United States Patent
Knappe et al.

(10) Patent No.: US 8,329,152 B2
(45) Date of Patent: Dec. 11, 2012

(54) SMOOTH STYLING AGENTS

(75) Inventors: Thorsten Knappe, Schenefeld (DE); Helga Van Flodrop, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/009,005

(22) Filed: Jan. 19, 2011

(65) Prior Publication Data
US 2011/0110878 A1    May 12, 2011

Related U.S. Application Data

(63) Continuation of application No. PCT/EP2009/058106, filed on Jun. 29, 2009.

(30) Foreign Application Priority Data

Jul. 21, 2008 (DE) .......................... 10 2008 034 102

(51) Int. Cl.
*A61Q 5/06* (2006.01)
*A61Q 5/12* (2006.01)
*A61K 8/00* (2006.01)

(52) U.S. Cl. .................................. 424/70.12; 442/70.15

(58) Field of Classification Search ........................ None
See application file for complete search history.

(56) References Cited

U.S. PATENT DOCUMENTS

| | | | |
|---|---|---|---|
| 3,753,968 A | | 8/1973 | Ward |
| 5,132,443 A | * | 7/1992 | Traver et al. .................. 556/425 |
| 5,227,164 A | * | 7/1993 | Lundmark ..................... 424/401 |
| 5,254,333 A | * | 10/1993 | Kajino et al. ............... 424/70.11 |
| 5,470,551 A | * | 11/1995 | Dubief et al. ............... 424/70.12 |
| 5,750,122 A | * | 5/1998 | Evans et al. .................... 424/401 |
| 5,773,595 A | | 6/1998 | Weuthen et al. |
| 6,149,898 A | | 11/2000 | Peffly et al. |
| 6,235,913 B1 | | 5/2001 | Raths et al. |
| 7,332,466 B2 | | 2/2008 | Schmid et al. |
| 7,462,363 B2 | * | 12/2008 | Braun et al. ................... 424/401 |
| 2006/0269490 A1 | * | 11/2006 | Braun et al. ...................... 424/59 |
| 2008/0312343 A1 | * | 12/2008 | Braun et al. ............... 514/772.3 |
| 2009/0069522 A1 | * | 3/2009 | Hessefort et al. .......... 526/307.5 |
| 2009/0074686 A1 | * | 3/2009 | Braun et al. .................... 424/59 |

FOREIGN PATENT DOCUMENTS

| | | |
|---|---|---|
| WO | 9213829 A1 | 8/1992 |
| WO | 2006018328 A2 | 2/2006 |
| WO | 2009016017 A2 | 2/2009 |

OTHER PUBLICATIONS

Gottschalck, T.E. et al. "International Cosmetic Ingredient Dictionary and Handbook." The Cosmetic, Toiletry and Fragrance Association, vol. 2, col. 3, 2006, p. 2161, XP002619200.

"International Cosmetic Ingredient Dictionary and Handbook." The Cosmetic, Toiletry, and Fragrance Association, seventh edition, 1997.

* cited by examiner

*Primary Examiner* — Robert A Wax
*Assistant Examiner* — Olga V Tcherkasskaya
(74) *Attorney, Agent, or Firm* — David LeCroy

(57) ABSTRACT

Agents for temporarily shaping keratin fibers having a very high degree of hold. These agents impart a feeling of providing flexible and conditioned hair while also being pleasant to the touch. Agents according to the invention contain, in a cosmetically acceptable carrier, at least one copolymer A having at least one structural unit according to formula (I), and at least one further structural unit according to formula (II), wherein $X^+$ is a physiologically acceptable cation, and further contains at least one further structural unit according to formula (III) and at least one silicone oil and/or silicone rubber.

14 Claims, No Drawings

SMOOTH STYLING AGENTS

CROSS REFERENCE TO RELATED APPLICATIONS

The present application is a continuation of International Patent Application No. PCT/EP2009/058106 filed 29 Jun. 2009, which claims priority to German Patent Application No. 10 2008 034 102.9 filed 21 Jul. 2008, both of which are incorporated herein by reference.

The present invention relates to agents for the temporary deformation of keratinic fibers, containing a combination of polymers with further specific ingredients; use of these agents for the temporary deformation of keratinic fibers; and to a corresponding method.

"Keratinic fibers" are understood to refer to all animal hair (e.g., wool, horsehair, angora wool, furs, feathers) and products or textiles produced therefrom. Preferably, however, the keratinic fibers are human hairs.

An attractive-looking hairstyle is generally regarded these days as an indispensable element of a well-groomed appearance. Considering fashion trends, more and more hairstyles regarded as chic are ones that, for many types of hair, can be constructed, or maintained for a longer period of time (e.g., up to several days) with only the use of setting ingredients. Hair treatment agents that provide permanent or temporary shaping of the hair therefore play an important role. Temporary shaping actions that are intended to yield good hold without impairing the hair's healthy appearance (e.g., its shine) can be achieved, for example, using hair sprays, hair waxes, hair gels, hair foams, blow-dry waves, etc.

Corresponding agents for temporary shaping usually contain synthetic polymers as a shaping component. Preparations containing a dissolved or dispersed polymer can be applied onto hair by propellant gases or by way of a pump mechanism. Hair gels and hair waxes in particular, however, are generally not applied directly onto the hair but rather distributed in the hair by a comb or the hands.

The most important property of an agent for the temporary deformation of keratinic fibers (hereinafter also called a styling agent) is to impart the strongest possible hold to the treated fibers in the shape that is generated. If the keratinic fibers involved are human hairs, terms also used are a strong "hairstyle hold" or a high "degree of hold" of the styling agent. The hairstyle hold is determined substantially by the nature and quantity of the synthetic polymer used, although the further constituents of the styling agent can also have an influence.

In addition to a high degree of hold, styling agents must also meet a large number of additional requirements. These can be subdivided generally into properties on the hair; properties of the particular formulation (e.g., properties of the foam, gel, or sprayed aerosol); and properties that relate to the handling of the styling agent, the properties on the hair being of particular importance. Moisture resistance, low tack, and a balanced conditioning effect may be mentioned in particular. In addition, a styling agent should be universally usable for, if possible, all types of hair. A high degree of hold is often undesirably associated with a highly brittle hairstyle. Hair treated with the corresponding styling agent is stiff, brittle, and appears to be unnaturally solid. As a result, it also feels rough and poorly cared for. In addition, in such cases the polymer film left behind by the agents upon application to the hair is so inflexible that it breaks under stress. This results in the formation of so-called film plaques (i.e., residues that detach upon movement of the hair) and give the impression that the user of the corresponding styling agent has dandruff.

A further problem is that product consistency of such products is viewed negatively by the user, since these products are seen as viscous, tacky, and difficult to apply.

The present invention, therefore, provides an agent for temporary deformation of keratinic fibers that is notable for a very high degree of hold with no sacrifice in flexibility and conditioned hair feel, as well as pleasant product feel.

It has now been discovered, surprisingly, that styling products having a high degree of hold and a pleasant well-cared-for feel in the hair can be made available by incorporating into the agents a combination of specific polymers with silicones.

A first subject of the present invention is therefore a cosmetic agent containing, in a cosmetically acceptable carrier— a) at least one copolymer A containing at least one structural unit according to formula (I)

at least one structural unit according to formula (II) and

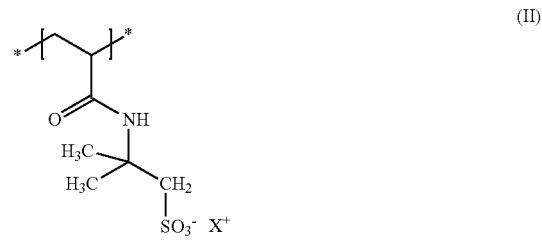

at least one structural unit according to formula (III)

wherein $X^+$ is a physiologically compatible cation, and
b) at least one silicone oil and/or silicone gum.

Agents according to the present invention contain, as a first component, a polymer constructed from at least three different monomers according to formulae (I), (II), and (III). Further monomers can additionally be polymerized in.

The first monomer present in copolymer A is sodium acrylate (i.e., the sodium salt of acrylic acid). In addition, acrylic acid can also be present in the polymers as a further monomeric constituent, but this is not obligatorily necessary according to the present invention.

The second monomer present in copolymer A is 2-methyl-2[(1-oxo-2-propenyl)amino]-1-propanesulfonic acid (AMPS), which can be present in a partly or entirely neutralized form. $Na^+$ and $NH_4^+$ are usually preferred as cations.

The third monomer that is contained in copolymer A is dimethylacrylamide. Copolymers A can be described by the general formula—

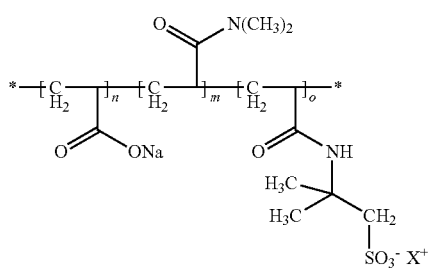

wherein indices m and n and o vary according to the molecular weight of the polymer and are not intended to indicate that these are obligatorily block copolymers. Structural units of formulas (I), (II), and (III) can instead also be present in statistically distributed fashion in the molecule.

The monomers of formulas (I), (II), and (III) are contained in copolymers A preferably in an amount and with a distribution such that copolymer A has a molecular weight in the range of from 5 to 1000 kDa. Preferred agents according to the present invention contain copolymer(s) A having molecular weights from 10 to 750 kDa, preferably from 25 to 500 kDa, more preferably from 50 to 400 kDa, and in particular from 70 to 250 kDa.

Preferably, the monomers of formulas (I), (II), and (III) are present in copolymer A within certain limits. Preferred agents according to the present invention contain copolymer(s) A having— to 90 mol %, preferably 15 to 85 mol % and particularly 20 to 80 mol %, monomers of formula (I), 5 to 85 mol %, preferably 7.5 to 80 mol % and particularly 10 to 60 mol %, monomers of formula (II), and 5 to 85 mol %, preferably 10 to 80 mol % and particularly 15 to 70 mol %, monomers of formula (III).

Regardless of whether the agents according to the present invention contain one or more copolymers A, it is preferred to use copolymers A within specific amounts. Preferred in this context are agents containing, based on total weight of the ready-to-use agent, 0.1 to 10 wt %, preferably 0.5 to 7.5 wt %, and particularly 1 to 5 wt % copolymer(s) A.

Very particularly preferably, compositions according to the present invention contain copolymer A in the form of a self-invertible inverse polymer latex containing an oil phase, a water phase, at least one oil-in-water emulsifier, and at least one branched or crosslinked polyelectrolyte (=copolymer A), which represents a copolymer having at least one monomer having a strong acid function and at least one further monomer that is neutral or contains a weak acid function.

A feature common to all the aforesaid inverse polymer latexes is that they contain at least one oil, preferably chosen from white mineral oils, squalane, isohexadecane, and (optionally hydrogenated) polyisobutene, as well as at least one oil-in-water emulsifier chosen from ethylene oxide adducts of sorbitan oleate, castor oil (which is hardened if desired), sorbitan laurate, and lauryl alcohol, and furthermore chosen from polyethylene-oxide-free oil-in-water emulsifier class of C6 to C22 fatty alcohol glucose ethers, particularly caprinic glucoside, caprylic glucoside, capric glucoside, lauric glucoside, myristic glucoside, cetyl glucoside, stearyl glucoside, arachidyl glucoside, behenyl glucoside, particularly preferably caprylic glucoside and capric glucoside. Preferred compositions according to the present invention accordingly have an oil phase of the inverse polymer latex containing at least one oil chosen from white mineral oils, squalane, isohexadecane, and (optionally hydrogenated) polyisobutene. Further preferred compositions according to the present invention have an oil-in-water emulsifier present in the inverse polymer latex chosen from ethylene oxide adducts of sorbitan oleate, castor oil (which is hardened if desired), sorbitan laurate, and lauryl alcohol, and from caprylic glucoside and capric glucoside.

Thickening polymer latexes to be used in preferred fashion according to the present invention preferably have a polymer content (of copolymer A) from 30 to 90 wt %, preferably 35 to 75 wt %, and particularly preferably 40 to 60 wt %, based on the entire latex. Polymer content of the latex is largely significant, however, for the manufacture of compositions according to the present invention (e.g., with regard to miscibility or dispensing characteristics). For actual compositions according to the present invention it is the polymer content itself, based on the composition according to the present invention, that is significant (see above).

According to the present invention, copolymer A is used particularly preferably in the form of a self-invertible inverse polymer latex that contains, in addition to copolymer A, isohexadecane as an oil phase and sorbitan monostearate as an emulsifier.

Agents according to the present invention contain as a second ingredient at least one silicone oil and/or silicone gum. Preferred agents contain at least one silicone, preferably a silicone chosen from among— i) polyalkylsiloxanes, polyarylsiloxanes, polyalkylarylsiloxanes, which are volatile or nonvolatile, straight-chain, branched, or cyclic, crosslinked or not crosslinked;

ii) polysiloxanes having in their general structure one or more organofunctional groups chosen from among substituted or unsubstituted aminated groups; (per)fluorinated groups; thiol groups; carboxylate groups; hydroxylated groups; alkoxylated groups; acyloxyalkyl groups; amphoteric groups; bisulfite groups; hydroxyacylamino groups; carboxy groups; sulfonic acid groups; and sulfate or thiosulfate groups;

iii) linear polysiloxane (A)-polyoxyalkylene (B) block copolymers of the $(A-B)_n$ type, where $n>3$;

iv) grafted silicone polymers having a non-silicone-containing organic backbone made of an organic main chain formed from organic monomers having no silicone, onto which, in the chain and optionally at least one end of the chain, at least one polysiloxane macromer has been grafted;

v) grafted silicone polymers having a polysiloxane backbone onto which have been grafted non-silicone-containing organic monomers having a polysiloxane main chain onto which, in the chain and optionally at least one of its ends, at least one organic macromer that contains no silicone has been grafted;

or mixtures thereof.

Agents particularly preferred according to the present invention contain silicone(s) preferably in quantities from 0.1 to 10 wt %, more preferably from 0.25 to 7 wt %, and in particular from 0.5 to 5 wt %, based in each case on the entire agent.

Useful silicone oils or silicone gums include dialkyl- and alkylarylsiloxanes, for example, dimethylpolysiloxane and methylphenylsiloxane, as well as alkoxylated, quaternized, or also anionic derivatives thereof. Cyclic and linear polydialkylsiloxanes, alkoxylated and/or aminated derivatives thereof, dihydroxylpolydimethylsiloxanes, and polyphenylalkylsiloxanes are preferred.

Silicone oils produce a very wide variety of effects. For example, they simultaneously influence dry and wet combability, the feel of dry and wet hair, and gloss. The skilled artisan understands the term "silicone oils" to refer to several structures of organosilicon compounds. These include firstly the dimethiconols (S1). These can be both linear and branched, and also cyclic or cyclic and branched. Linear dimethiconols can be represented by the following structural formula (S1-I)—

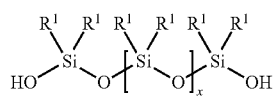
(S1-I)

Branched dimethiconols can be represented by the structural formula (S1-II)—

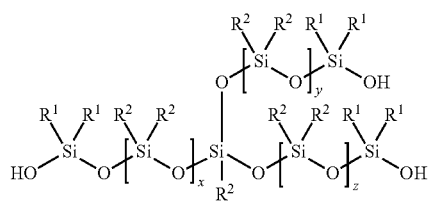
(S1-II)

$R^1$ and $R^2$ each mutually independently represent hydrogen, a methyl residue, a $C_2$ to $C_{30}$ linear, saturated or unsaturated hydrocarbon residue, a phenyl residue, and/or an aryl residue. Non-limiting examples of residues represented by $R^1$ and $R^2$ include alkyl residues such as methyl, ethyl, propyl, isopropyl, butyl, isobutyl, pentyl, isopentyl, neopentyl, amyl, isoamyl, hexyl, isohexyl and the like; alkenyl residues such as vinyl, halovinyl, alkylvinyl, allyl, haloallyl, alkylallyl; cycloalkyl residues such as cyclobutyl, cyclopentyl, cyclohexyl, and the like; phenyl residues, benzyl residues, halogenated hydrocarbon residues such as 3-chloropropyl, 4-bromobutyl, 3,3,3-trifluoropropyl, chlorocyclohexyl, bromophenyl, chlorophenyl, and the like, and sulfur-containing residues such as mercaptoethyl, mercaptopropyl, mercaptohexyl, mercaptophenyl, and the like. Preferably, $R^1$ and $R^2$ are an alkyl residue containing 1 to approximately 6 carbon atoms, and more preferably $R^1$ and $R^2$ are methyl. The numbers x, y, and z are integers and range, mutually independently, from 0 to 50,000. Molecular weights of the dimethiconols are from 1000 D to 10,000,000 D. The viscosities are from 100 to 10,000,000 cPs, measured at 25° C. using a glass capillary viscosimeter in accordance with Dow Corning Corporate Test Method CTM 0004 of Jul. 20, 1970. Preferred viscosities are from 1000 to 5,000,000 cPs; very particularly preferred viscosities are from 10,000 to 3,000,000 cPs. The most preferred range is from 50,000 to 2,000,000 cPs.

The following commercial products are examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401DC (all the aforesaid Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all the aforesaid Dow Corning Corporation), Dub Gel SI 1400 (Stearinerie Dubois Fils), HVM 4852 Emulsion (Crompton Corporation), Jeesilc 6056 (Jeen International Corporation), Lubrasil, Lubrasil DS (both Guardian Laboratories), Nonychosine E, Nonychosine V (both Exsymol), SanSurf Petrolatum-25, Satin Finish (both Collaborative Laboratories, Inc.), Silatex-D30 (Cosmetic Ingredient Resources), Silsoft 148, Silsoft E-50, Silsoft E-623 (all the aforesaid Crompton Corporation), SM555, SM2725, SM2765, SM2785 (all the aforesaid GE Silicones), Taylor T-Sil CD-1, Taylor TME-4050E (all Taylor Chemical Company), TH V 148 (Crompton Corporation), Tixogel CYD-1429 (Sud-Chemie Performance Additives), Wacker-Belsil CM 1000; Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all the aforesaid Wacker-Chemie GmbH).

Dimethicones (S2) comprise the second group of silicones that can be used according to the present invention. They can be both linear and branched, as well as cyclic or cyclic and branched. Linear dimethicones can be represented by the following structural formula (S2-I)—

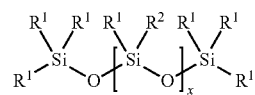
(S2-I)

Branched dimethicones can be represented by the structural formula (S2-II)—

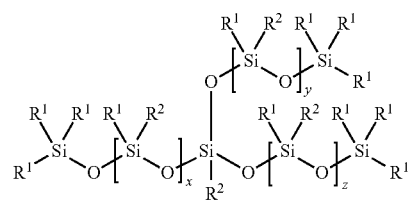
(S2-II)

$R^1$ and $R^2$ are each, mutually independently, hydrogen, a methyl residue, a $C_2$ to $C_{30}$ linear, saturated or unsaturated hydrocarbon residue, a phenyl residue, and/or an aryl residue. Non-limiting examples of residues represented by $R^1$ and $R^2$ include alkyl residues such as methyl, ethyl, propyl, isopropyl, butyl, isobutyl, pentyl, isopentyl, neopentyl, amyl, isoamyl, hexyl, isohexyl and the like; alkenyl residues such as vinyl, halovinyl, alkylvinyl, allyl, haloallyl, alkylallyl; cycloalkyl residues such as cyclobutyl, cyclopentyl, cyclohexyl, and the like; phenyl residues, benzyl residues, halogenated hydrocarbon residues such as 3-chloropropyl, 4-bromobutyl, 3,3,3-trifluoropropyl, chlorocyclohexyl, bromophenyl, chlorophenyl, and the like, and sulfur-containing residues such as mercaptoethyl, mercaptopropyl, mercaptohexyl, mercaptophenyl, and the like. Preferably, $R^1$ and $R^2$ are an alkyl residue containing 1 to approximately 6 carbon atoms, and particularly preferably $R^1$ and $R^2$ are methyl. The numbers x, y, and z are integers and range, mutually independently, from 0 to 50,000. Molecular weights of the dimethicones are from 1000 D to 10,000,000 D. Viscosities are from 100 to 10,000,000 cPs, measured at 25° C. using a glass capillary viscosimeter in accordance with Dow Corning Corporate Test Method CTM 0004 of Jul. 20, 1970. Preferred viscosities are from 1000 and 5,000,000 cPs; particularly preferred viscosities are from 10,000 to 3,000,000 cPs. Very particularly preferably, the viscosity is in the range from 50,000 to 2,000,000 cPs.

Dimethicone copolyols (S3) constitute a further group of silicones that are suitable. Dimethicone copolyols can be represented by the following structural formulas—

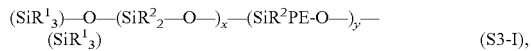 (S3-I),

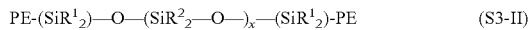 (S3-II)

Branched dimethicone copolyols can be represented by the structural formula (S3-III)—

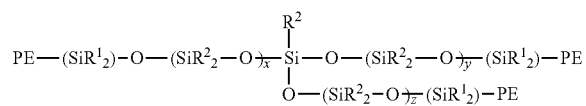 (S3-III)

or by the structural formula (S3-IV)—

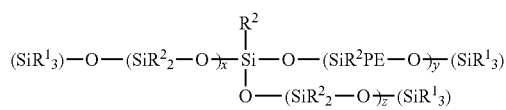 (S3-IV)

$R^1$ and $R^2$ each represent, mutually independently, hydrogen, a methyl residue, a $C_2$ to $C_{30}$ linear, saturated or unsaturated hydrocarbon residue, a phenyl residue, and/or an aryl residue. Non-limiting examples of the residues represented by $R^1$ and $R^2$ include alkyl residues such as methyl, ethyl, propyl, isopropyl, butyl, isobutyl, pentyl, isopentyl, neopentyl, amyl, isoamyl, hexyl, isohexyl and the like; alkenyl residues such as vinyl, halovinyl, alkylvinyl, allyl, haloallyl, alkylallyl; cycloalkyl residues such as cyclobutyl, cyclopentyl, cyclohexyl, and the like; phenyl residues, benzyl residues, halogenated hydrocarbon residues such as 3-chloropropyl, 4-bromobutyl, 3,3,3-trifluoropropyl, chlorocyclohexyl, bromophenyl, chlorophenyl, and the like, and sulfur-containing residues such as mercaptoethyl, mercaptopropyl, mercaptohexyl, mercaptophenyl, and the like. $R^1$ and $R^2$ are preferably an alkyl residue containing 1 to approximately 6 carbon atoms, and more preferably $R^1$ and $R^2$ are methyl. PE is a polyoxyalkylene residue. Preferred polyoxyalkylene residues are derived from ethylene oxide, propylene oxide, and glycerol. The numbers x, y, and z are integers and range, mutually independently, from 0 to 50,000. Molecular weights of the dimethicones are from 1000 D to 10,000,000 D. Viscosities are from 100 to 10,000,000 cPs, measured at 25° C. using a glass capillary viscosimeter in accordance with Dow Corning Corporate Test Method CTM 0004 of Jul. 20, 1970. Preferred viscosities are from 1000 to 5,000,000 cPs; very particularly preferred viscosities are from 10,000 to 3,000,000 cPs. The most preferred range is from 50,000 to 2,000,000 cPs. Corresponding dimethicone copolyols are commercially obtainable and are marketed, for example, by the Dow Corning company under the designation Dow Corning® 5330 Fluid.

The present invention also, of course, encompasses the fact that the dimethiconols, dimethicones, and/or dimethicone copolymers can already be present as an emulsion. The corresponding emulsion of the dimethiconols, dimethicones, and/or dimethicone copolyols can be manufactured both after manufacture of the corresponding dimethiconols, dimethicones, and/or dimethicone copolyols, from them and using usual emulsification methods known to the skilled artisan. For this purpose both cationic, anionic, nonionic, or zwitterionic surfactants and emulsifiers can be used, as auxiliaries, as adjuvants for manufacture of the corresponding emulsions. Emulsions of the dimethiconols, dimethicones, and/or dimethicone copolyols can also be manufactured directly by an emulsion polymerization method. Such methods, too, are very familiar to the skilled artisan.

If the dimethiconols, dimethicones, and/or dimethicone copolyols are used as an emulsion, the droplet size of the emulsified particles is then, according to the present invention, 0.01 to 10,000 μm, preferably 0.01 to 100 μm, particularly preferably 0.01 to 20 μm, and very particularly preferably 0.01 to 10 μm. The particle size is determined using the light-scattering method.

If branched dimethiconols, dimethicones, and/or dimethicone copolyols are used, this is to be understood to mean that the branching is greater than a random branching that occurs randomly as a result of contaminants in the respective monomers. "Branched" dimethiconols, dimethicones, and/or dimethicone copolyols are therefore to be understood, for purposes of the present invention, to mean that the degree of branching is greater than 0.01%. A degree of branching greater than 0.1% is preferred, and very particularly preferably it is greater than 0.5%. The degree of branching is determined from the ratio of unbranched monomers to the branching monomers (i.e., the amount of tri- and tetrafunctional siloxanes). Both low-branching and high-branching dimethiconols, dimethicones, and/or dimethicone copolyols can be particularly preferred according to the present invention.

Suitable silicones further include aminofunctional silicones (S4), particularly silicones grouped under the INCI name Amodimethicone. These are to be understood as silicones having at least one, optionally substituted, amino group.

Such silicones can be described, for example, by the formula—

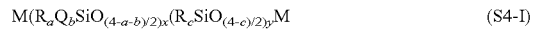 (S4-I)

wherein R is a hydrocarbon or hydrocarbon residue having 1 to approximately 6 carbon atoms, Q is a polar residue of the general formula —$R^1Z$, wherein $R^1$ is a divalent bonding group that is bound to hydrogen and to the Z residue, assembled from carbon and hydrogen atoms, carbon, hydrogen, and oxygen atoms, or carbon, hydrogen, and nitrogen atoms; and Z is an organic aminofunctional residue having at least one aminofunctional group; "a" assumes values in the range from approximately 0 to approximately 2; "b" assumes values in the range from approximately 1 to approximately 3; "a"+"b" is less than or equal to 3; "c" is a number in the range from approximately 1 to approximately 3; x is a number in the range from 1 to approximately 2,000, preferably from approximately 3 to approximately 50, and most preferably from approximately 3 to approximately 25; y is a number in the range from approximately 20 to approximately 10,000, preferably from approximately 125 to approximately 10,000, and most preferably from approximately 150 to approximately 1,000; and M is a suitable silicone terminal group known in the art, preferably trimethylsiloxy. Non-limiting examples of residues represented by R include alkyl residues such as methyl, ethyl, propyl, isopropyl, isopropyl, butyl, isobutyl, amyl, isoamyl, hexyl, isohexyl and the like; alkenyl residues such as vinyl, halovinyl, alkylvinyl, allyl, haloallyl, alkylallyl; cycloalkyl residues such as cyclobutyl, cyclopentyl, cyclohexyl and the like; phenyl residues, benzyl residues, halogenated hydrocarbon residues such as 3-chloropropyl, 4-bromobutyl, 3,3,3-trifluoropropyl, chlorocyclohexyl, bromophenyl, chlorophenyl and the like; and sulfur-containing residues such as mercaptoethyl, mercaptopropyl, mercaptohexyl, mercaptophenyl and the like. R preferably is an alkyl residue having 1 to approximately 6 carbon atoms, and R is most preferably methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)$ $OCH_2$—, —$(CH_2)_3C(O)OCH_2CH_2$—, —$C_6H_4C_6H_4$—, —$C_6H_4CH_2C_6H_4$—, and —$(CH_2)_3C(O)SCH_2CH_2$—.

Z is an organic aminofunctional residue having at least one functional amino group. One possible formula for Z is $NH(CH_2)_zNH_2$, wherein z is an integer from 1 to 50. Another possible formula for Z is —$NH(CH_2)_zNH(CH_2)_{zz}$, wherein both z and zz are, mutually independently, an integer from 1 to 50. This structure includes diamino ring structures such as piperazinyl. Z is particularly preferably a —$NHCH_2CH_2NH_2$ residue. Another possible formula for Z is —$N(CH_2)_zNX^1X^2$ or —$NX^1X^2$, wherein $X^1$ and $X^2$ are, mutually independently in each case, hydrogen or a hydrocarbon residue having from 1 to approximately 6 carbon atoms. Very particularly preferably, Q is a polar aminofunctional residue of the formula —$CH_2CH_2CH_2NHCH_2CH_2NH_2$.

The molar ratio of $R_aQ_bSiO_{(4-a-b)/2}$ units to $R_cSiO_{(4-c)/2}$ units is in the range from approximately 1:2 to 1:65, preferably from approximately 1:5 to approximately 1:65, and particularly preferably from approximately 1:15 to approximately 1:20. If one or more silicones of the above formula are used, the different variable substituents in the above formula can then differ in the different silicone components that are present in the silicone mixture.

Preferred aminofunctional silicones correspond to the formula (S4-II)—

$$R'_aG_{3-a}-Si(OSiG_2)_n-(OSiG_bR'_{2-b})_m-O-SiG_{3-a}-R'_a \quad (S4-II)$$

wherein
G is hydrogen, a phenyl group, —OH, —O—$CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)$ $CH_2CH_3$, —$C(CH_3)_3$;
a is a number from 0 to 3, in particular 0;
b is a number from 0 to 1, in particular 1,
m and n are numbers whose sum (m+n) is from 1 to 2000, preferably from 50 to 150; n preferably is a value from 0 to 1999 and particularly from 49 to 149, and m preferably is a value from 1 to 2000, particularly from 1 to 10;
R' is a monovalent residue selected from —N(R")—$CH_2$—$CH_2$—$N(R")_2$, —$N(R")_2$, —$N^+(R")_3A^-$, —$N^+H$ $(R")_2A^-$, —$N^+H_2(R")A^-$, —$N(R")$—$CH_2$—$CH_2$—$N^+$ $R"H_2A^-$, with each R" representing identical or different residues of hydrogen, phenyl, benzyl, $C_{1-20}$ alkyl residues, preferably —$CH_3$, —$CH_2CH_3$, —$CH_2CH_2CH_3$, —$CH(CH_3)_2$, —$CH_2CH_2H_3$, —$CH_2CH(CH_3)_2$, —$CH(CH_3)CH_2CH_3$, —$C(CH_3)_3$; and $A^-$ is an anion that is preferably chosen from chloride, bromide, iodide, or methosulfate.

Particularly preferred aminofunctional silicones correspond to formula (S4-III)—

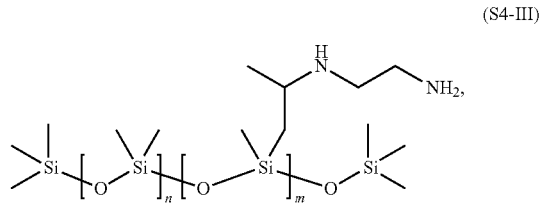

(S4-III)

wherein m and n are numbers whose sum (m+n) is from 1 to 2000, preferably from 50 to 150, n preferably assuming values from 0 to 1999, particularly from 49 to 149, and m preferably assuming values from 1 to 2000, particularly from 1 to 10.

These silicones are referred to according to the INCI declaration as Trimethylsilylamodimethicone.

Also particularly preferred are aminofunctional silicones of formula (S4-IV)—

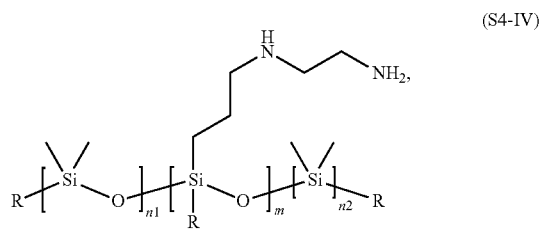

(S4-IV)

wherein R is —OH, —O—$CH_3$, or a —$CH_3$ group; m, n1, and n2 are numbers whose sum (m+n1+n2) is from 1 to 2000, preferably from 50 to 150, the sum (n1+n2) preferably assuming values from 0 to 1999 and particularly from 49 to 149, and m preferably assuming values from 1 to 2000, in particular from 1 to 10.

These silicones are referred to according to the INCI declaration as Amodimethicone, and are available, for example, in the form of an emulsion as the commercial product Dow Corning® 949, mixed with a cationic and a nonionic surfactant.

Useful aminofunctional silicones preferably have an amine number of 0.25 meq/g or greater, more preferably 0.3 meq/g or greater, and particularly preferably 0.4 meq/g or greater. The amine number represents the milliequivalent of amine per gram of aminofunctional silicone. It can be ascertained by titration, and is also indicated with the unit "mg KOH/g".

Further suitable silicones include—
oligomeric polydimethylcyclosiloxanes (INCI name: Cyclomethicone), particularly tetrameric and pentameric compounds, commercially available from Dow Corning under the tradenames DC 245 Fluid, DC 344, and DC 345, respectively;
hexamethyldisiloxane (INCI name: Hexamethyldisiloxane), for example, the product available under the tradename Abil® K 520;
polyphenylmethylsiloxanes (INCI name: Phenyl Trimethicone), for example, the commercial product DC 556 Cosmetic Grade Fluid of Dow Corning;
esters and partial esters of the silicone-glycol copolymers, such as those marketed, for example, by the Fanning company under the commercial designation Fancorsil® LIM (INCI name: Dimethicone Copolyol Meadowfoamate);

anionic silicone oils such as the product Dow Corning® 1784.

According to a preferred embodiment, the agent according to the present invention contains at least two different silicone derivatives, particularly a combination of a volatile and a non-volatile silicone. Silicones that exhibit volatility equal to or greater than the volatility of cyclic pentameric dimethylsiloxane are "volatile" for purposes of the invention. Such combinations are also available commercially (e.g., Dow Corning® 1401, Dow Corning® 1403, and Dow Corning® 1501, each a mixture of a cyclomethicone and a dimethiconol).

Preferred mixtures of different silicones include dimethicones and dimethiconols, linear dimethicones, and cyclic dimethiconols. A very particularly preferred mixture of silicones is made up of at least one cyclic dimethiconol and/or dimethicone, at least one further non-cyclic dimethicone and/or dimethiconol, and at least one aminofunctional silicone.

If different silicones are used as a mixture, the mixing ratio is largely variable. Preferably, however, all silicones used for mixing are utilized at a ratio of from 5:1 to 1:5 in the case of a binary mixture. A ratio from 1:3 to 3:1 is particularly preferred. Very particularly preferred mixtures contain all silicones in the mixture very largely at a ratio of approximately 1:1, based on total quantity used in wt %.

Particularly preferred silicones are described below. Particularly preferred agents according to the present invention contain at least one silicone of formula (Si-I)—

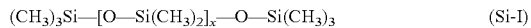

(CH$_3$)$_3$Si—[O—Si(CH$_3$)$_2$]$_x$—O—Si(CH$_3$)$_3$     (Si-I)

wherein x is a number from 0 to 100, preferably from 0 to 50, more preferably from 0 to 20, and particularly 0 to 10. These silicones are referred to in INCI nomenclature as Dimethicone. (CH$_3$)$_3$Si—O—Si(CH$_3$)$_3$ and/or (CH$_3$)$_3$Si—O—(CH$_3$)$_2$Si—O—Si(CH$_3$)$_3$ and/or (CH$_3$)$_3$Si—[O—(CH$_3$)$_2$Si]$_2$—O—Si(CH$_3$)$_3$ are particularly preferred for use. Mixtures of the aforesaid silicones can also be present in agents according to the present invention.

Preferred silicones usable according to the present invention have viscosities from 0.2 to 2 mm$^2$s$^{-1}$ at 20° C.; silicones having viscosities from 0.5 to 1 mm$^2$s$^{-1}$ are particularly preferred.

Particularly preferred agents according to the present invention contain one or more aminofunctional silicones. Such silicones can be described, for example, by the formula—

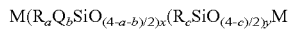

M(R$_a$Q$_b$SiO$_{(4-a-b)/2}$)$_x$(R$_c$SiO$_{(4-c)/2}$)$_y$M wherein R is a hydrocarbon or hydrocarbon residue having 1 to approximately 6 carbon atoms, Q is a polar residue of the general formula —R$^1$HZ, wherein R$^1$ is a divalent bonding group that is bound to hydrogen and to the Z residue and assembled from carbon and hydrogen atoms, carbon, hydrogen, and oxygen atoms, or carbon, hydrogen, and nitrogen atoms, and Z is an organic aminofunctional residue having at least one aminofunctional group; "a" is a value in the range from approximately 0 to approximately 2; "b" is a value in the range from approximately 1 to approximately 3; "a"+"b" is less than or equal to 3; "c" is a number in the range from approximately 1 to approximately 3; x is a number in the range from 1 to approximately 2,000, preferably from approximately 3 to approximately 50, and most preferably from approximately 3 to approximately 25; y is a number in the range from approximately 20 to approximately 10,000, preferably from approximately 125 to approximately 10,000, and most preferably from approximately 150 to approximately 1,000; and M is a suitable silicone terminal group known in the art, preferably trimethylsiloxy. Non-limiting examples of residues represented by R include alkyl residues such as methyl, ethyl, propyl, isopropyl, isopropyl, butyl, isobutyl, amyl, isoamyl, hexyl, isohexyl and the like; alkenyl residues such as vinyl, halovinyl, alkylvinyl, allyl, haloallyl, alkylallyl; cycloalkyl residues such as cyclobutyl, cyclopentyl, cyclohexyl and the like; phenyl residues, benzyl residues, halocarbon residues such as 3-chloropropyl, 4-bromobutyl, 3,3,3-trifluoropropyl, chlorocyclohexyl, bromophenyl, chlorophenyl, and the like, and sulfur-containing residues such as mercaptoethyl, mercaptopropyl, mercaptohexyl, mercaptophenyl and the like. R is preferably an alkyl residue having 1 to approximately 6 carbon atoms, and R is most preferably methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—, and —(CH$_2$)$_3$C(O)SCH$_2$CH$_2$—.

Z is an organic aminofunctional residue containing at least one functional amino group. One possible formula for Z is NH(CH$_2$)$_z$NH$_2$, wherein z is 1 or more. Another possible formula for Z is —NH(CH$_2$)$_z$NH(CH$_2$)$_{zz}$NH, wherein both z and zz, mutually independently, are 1 or more. This structure encompasses diamino ring structures such as piperazinyl. Z is particularly preferably a —NHCH$_2$CH$_2$NH$_2$ residue. Another possible formula for Z is —N(CH$_2$)$_z$(CH$_2$)$_{zz}$NX$_2$ or —NX$_2$, wherein each X is selected, independently of X$_2$, from hydrogen and alkyl groups having 1 to 12 carbon atoms, and zz is 0.

Q is most preferably a polar aminofunctional residue of the formula —CH$_2$CH$_2$CH$_2$NHCH$_2$CH$_2$NH$_2$. In the formulae, "a" is a value in the range from approximately 0 to approximately 2, "b" is a value in the range from approximately 2 to approximately 3, "a"+"b" is less than or equal to 3, and "c" is a number in the range from approximately 1 to approximately 3. The molar ratio of R$_a$Q$_b$SiO$_{(4-a-b)/2}$ units to R$_c$SiO$_{(4-c)/2}$ units is in the range from approximately 1:2 to 1:65, preferably from approximately 1:5 to approximately 1:65, and most preferably from approximately 1:15 to approximately 1:20. If one or more silicones of the above formula are used, the different variable substituents in the above formula can then be different in the different silicone components present in the silicone mixture.

Preferred agents according to the present invention contain an aminofunctional silicone of formula (Si-II)—

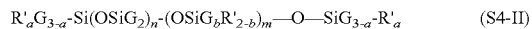

R'$_a$G$_{3-a}$-Si(OSiG$_2$)$_n$-(OSiG$_b$R'$_{2-b}$)$_m$—O—SiG$_{3-a}$-R'$_a$     (S4-II)

wherein
G is hydrogen, a phenyl group, —OH, —O—CH$_3$, —CH$_3$, O—CH$_2$CH$_3$, —CH$_2$CH$_3$, O—CH$_2$CH$_2$CH$_3$, —CH$_2$CH$_2$CH$_3$, O—CH(CH$_3$)$_2$, —CH(CH$_3$)$_2$, O—CH$_2$CH$_2$CH$_2$CH$_3$, —CH$_2$CH$_2$CH$_2$CH$_3$, O—CH$_2$CH(CH$_3$)$_2$, —CH$_2$CH(CH$_3$)$_2$, O—CH(CH$_3$)CH$_2$CH$_3$, —CH(CH$_3$)CH$_2$CH$_3$, O—C(CH$_3$)$_3$, —C(CH$_3$)$_3$;
a is a number from 0 to 3, in particular 0;
b is a number from 0 to 1, in particular 1,
m and n are numbers whose sum (m+n) is from 1 to 2000, preferably from 50 to 150, n preferably assuming a value from 0 to 1999 and in particular from 49 to 149, and m preferably assuming a value from 1 to 2000, in particular from 1 to 10;

R' is a monovalent residue chosen from -Q-N(R")—CH$_2$—CH$_2$—N(R")$_2$, -Q-N(R")$_2$, -Q-N$^+$(R")$_3$A$^-$, -Q-N$^+$H(R")$_2$A$^-$, -Q-N$^+$H$_2$(R")A$^-$, -Q-N(R")—CH$_2$—CH$_2$—N$^+$R"H$_2$A$^-$, each Q representing a chemical bond, —CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, or —CH(CH$_3$)CH$_2$CH$_2$—, R" is identical or different residues of —H, phenyl, benzyl, C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, or —C(CH$_3$)$_3$, and A is an anion preferably chosen from chloride, bromide, iodide, or methosulfate.

Particularly preferred agents according to the present invention have at least one aminofunctional silicone of formula (Si-IIa)—

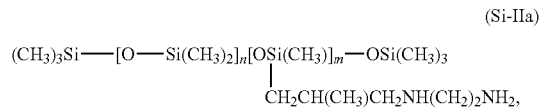

$$(CH_3)_3Si—[O—Si(CH_3)_2]_n[OSi(CH_3)]_m—OSi(CH_3)_3$$
$$\quad\quad\quad\quad\quad\quad\quad\quad | $$
$$\quad\quad\quad CH_2CH(CH_3)CH_2NH(CH_2)_2NH_2,$$

wherein m and n are numbers whose sum (m+n) is from 1 to 2000, preferably from 50 to 150, n preferably is a value from 0 to 1999 and in particular from 49 to 149, and m preferably is a value from 1 to 2000, in particular from 1 to 10.

These silicones are referred to according to the INCI declaration as Trimethylsilylamodimethicone.

Also particularly preferred are agents according to the present invention having an aminofunctional silicone of formula (Si-IIb)—

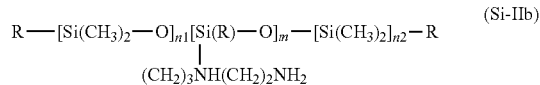

$$R—[Si(CH_3)_2—O]_{n1}[Si(R)—O]_m—[Si(CH_3)_2]_{n2}—R$$
$$\quad\quad\quad\quad\quad\quad\quad |$$
$$\quad\quad\quad\quad (CH_2)_3NH(CH_2)_2NH_2$$

wherein R is —OH, —O—CH$_3$ or a —CH$_3$ group; m, n1, and n2 are numbers whose sum (m+n1+n2) is equal to from 1 to 2000, preferably from 50 to 150, the sum (n1+n2) is a value preferably from 0 to 1999 and in particular from 49 to 149, and m is a value preferably from 1 to 2000, in particular from 1 to 10. These silicones are referred to according to the INCI declaration as Amodimethicone.

Regardless of which aminofunctional silicones are used, agents according to the present invention having an aminofunctional silicone whose amine number is above 0.25 meq/g, preferably above 0.3 meq/g, and in particular above 0.4 meq/g, are preferred. The amine number is, in this context, the milliequivalent amine per gram of the aminofunctional silicone. It can be ascertained by titration, and also indicated using the unit of "mg KOH/g".

Agents preferred according to the present invention contain, based on their weight, 0.01 to 10 wt %, preferably 0.1 to 8 wt %, more preferably 0.25 to 7.5 wt %, and in particular 0.5 to 5 wt % aminofunctional silicone(s).

Cyclic dimethicones referred to according to INCI as Cyclomethicone are also usable according to the present invention. Agents according to the present invention having at least one silicone of formula Si-III—

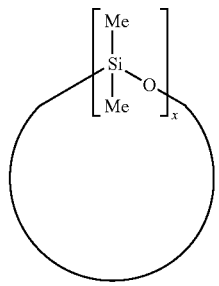

wherein x is a number from 3 to 200, preferably from 3 to 10, more preferably from 3 to 7, and in particular 3, 4, 5, or 6, are preferred here.

The silicones described above have a backbone constructed from Si—O—Si units. These Si—O—Si units can also be interrupted by carbon chains. Corresponding molecules are accessible via chain-lengthening reactions, and are preferably in the form of silicone-in-water emulsions.

Agents that are likewise preferred according to the present invention contain at least one silicone of formula Si-IV—

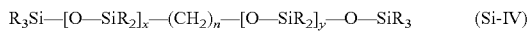

$$R_3Si—[O—SiR_2]_x—(CH_2)_n—[O—SiR_2]_y—O—SiR_3 \quad\quad (Si\text{-}IV)$$

wherein R is identical or different residues from the group —H, phenyl, benzyl, —CH$_2$—CH(CH$_3$)Ph, and C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$; x and y are a number from 0 to 200, preferably from 0 to 10, more preferably from 0 to 7, and in particular 0, 1, 2, 3, 4, 5, or 6, and n is a number from 0 to 10, preferably from 1 to 8, and in particular 2, 3, 4, 5, 6.

Agents according to the present invention preferably contain a film-forming polymer as a further ingredient. Particularly preferred agents according to the present invention contain, based on their weight, 0.1 to 25 wt % of at least one film former. Particularly preferred film formers that can be used in the agents according to the present invention are described below.

Particularly preferred agents according to the present invention contain at least one further copolymer B having at least one structural unit according to formula (B-I) and at least one structural unit of formula (B-II)—

wherein

R is a C$_1$ to C$_{30}$ alkyl group, a C$_1$ to C$_4$ aralkyl group, a C$_2$ to C$_6$ alkenyl group, or a C$_2$ to C$_6$ hydroxyalkyl group, X$^-$ is a physiologically compatible anion, and n is 1, 2 or 3 as the number of methylene units.

Film-forming and/or setting copolymers B are known. These copolymers have at least one structural unit according to formula (B-I) and at least one structural unit according to formula (B-II), and can further comprise additional structural units polymerized in during polymerization by addition of corresponding monomers.

Preferred groups R include —CH$_3$; —CH$_2$CH$_3$, —CH$_2$CH$_2$CH$_3$, CH(CH$_3$)$_2$, —(CH$_2$)$_3$CH$_3$, —CH$_2$—CH (CH$_3$)$_2$, CH(CH$_3$)CH$_2$CH$_3$, —C(CH$_3$)$_3$, —CH$_2$OH, —CH$_2$CH$_2$OH, —CH$_2$CH$_2$CH$_2$OH, —CH(OH)CH$_2$CH$_3$, —CH$_2$CH(OH)CH$_3$. X$^-$ is a physiologically compatible anion; preferred anions are chloride, bromide, iodide, sulfate, methosulfate, ethyl sulfate, tosylate and tetrafluoroborate.

In formula (B-II), n is the number of methylene groups. When n=1, formula (B-II) is a vinylpyrrolidone unit; when n=2 it is a vinylpiperidinone unit; and when n=3 it is a vinylcaprolactam unit. Particularly preferred agents according to the present invention contain as copolymer B a copolymer B1 having at least one structural unit according to formula (B-I) and at least one structural unit according to formula (B-II)—

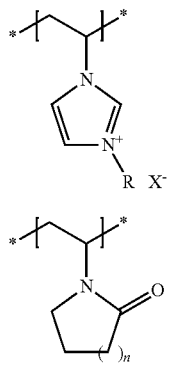

wherein R is a methyl group, X$^-$ is methosulfate, and n is 1 methylene unit.

Very particularly preferred copolymers B1 contain 10 to 30 mol %, preferably 15 to 25 mol %, and in particular 20 mol % structural units according to formula (B-I), and 70 to 90 mol %, preferably 75 to 85 mol %, and in particular 80 mol % structural units according to formula (B-II).

It is particularly preferred if copolymers B1 contain, in addition to polymer units resulting from incorporation into the copolymer of the aforesaid structural units according to formula (B-I) and (B-II), a maximum of 5 wt %, preferably a maximum of 1 wt % polymer units attributable to the incorporation of other monomers. Copolymers B1 are preferably constructed exclusively from structural units of formulas (B-I) and (B-II), and can be described by the general formula—

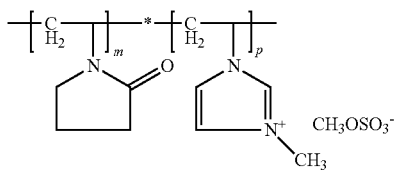

wherein m and n vary depending on the molecular weight of the polymer and are not intended to indicate that these are block copolymers. Structural units of formula (B-I) and formula (B-II) can instead be present in statistically distributed fashion in the molecule. N-methylvinylimidazole/vinylpyrrolidone copolymers of this kind are referred to in INCI nomenclature as Polyquaternium-44, and are obtainable, for example, from BASF under the trade name Luviquat® UltraCare. Agents particularly preferred according to the present invention contain a copolymer B1 having molecular weights within a specific range. Preferred are agents wherein copolymer B1 has a molecular weight from 50 to 400 kDa, preferably from 100 to 300 kDa, more preferably from 150 to 250 kDa, and in particular from 190 to 210 kDa.

In addition to or instead of copolymer(s) B1, agents according to the present invention can also contain copolymers B2 having, as additional structural units, structural units of formula (B-II) wherein n is the number 3. Further particularly preferred agents contain as copolymer B a copolymer B2 having at least one structural unit according to formula (B-I) and at least one structural unit of formula (B-II) where n=1, and at least one further structural unit of formula (B-II) where n=3—

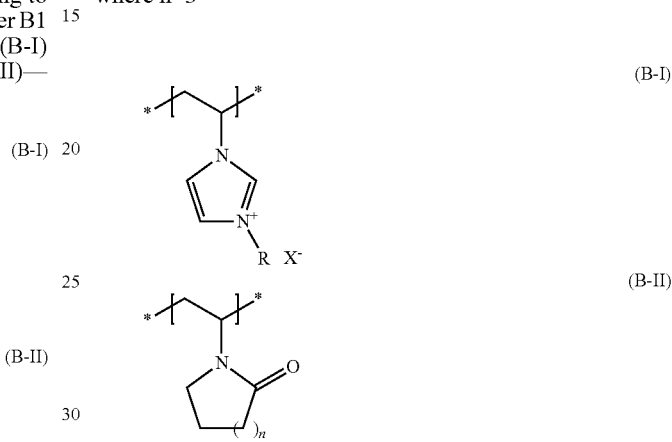

wherein R is a methyl group and X$^-$ is methosulfate. Here as well, it is particularly preferred if copolymers B2 contain, in addition to polymer units formed from incorporation into the copolymer of the aforesaid structural units according to formula (B-I) and (B-II), a maximum of 5 wt %, preferably a maximum of 1 wt % polymer units attributable to the incorporation of other monomers. Copolymers B2 are preferably constructed exclusively from structural units of formulas (B-I) and (B-II), and can be described by the general formula—

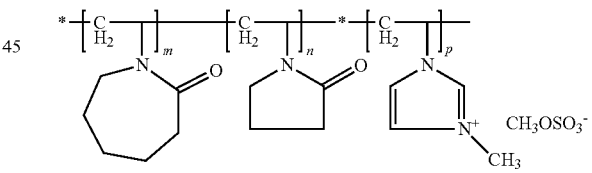

wherein m, n, and p vary depending on the molecular weight of the polymer and are not intended to indicate that these are block copolymers. Structural units of formula (B-I) and formula (B-II) can instead be present in statistically distributed fashion in the molecule.

N-methylvinylimidazole/vinylpyrrolidone/vinylcaprolactam copolymers of this kind are referred to in INCI nomenclature as Polyquaternium-46, and are obtainable, for example, from BASF under the trade name Luviquat® Hold.

Very particularly preferred copolymers B2 contain 1 to 20 mol %, preferably 5 to 15 mol %, and in particular 10 mol % structural units according to formula (B-I), and 30 to 50 mol %, preferably 35 to 45 mol %, and in particular 40 mol % structural units according to formula (B-II) where n=1, and 40 to 60 mol %, preferably 45 to 55 mol %, and in particular 60 mol % structural units according to formula (B-II) where n=3. Particularly preferred agents according to the present invention contain a copolymer B2 having molecular weights within a specific range. Preferred in this context are agents wherein copolymer B2 has a molecular weight from 100 to 1000 kDa, preferably from 250 to 900 kDa, more preferably from 500 to 850 kDa, and in particular from 650 to 710 kDa.

In addition to or instead of copolymer(s) B1 and/or B2, agents according to the present invention can also contain copolymers B3 having, as additional structural units, structural units of formula (B-II) wherein n is the number 3, as well as further distructural units from vinylimidazole units and further structural units from acrylamide units and/or methacrylamide units.

Further particularly preferred agents according to the present invention contain as copolymer B a copolymer B3 having at least one structural unit according to formula (B-I) and at least one structural unit of formula (B-II) and at least one structural unit of formula (B-III) and at least one structural unit of formula (B-IV)—

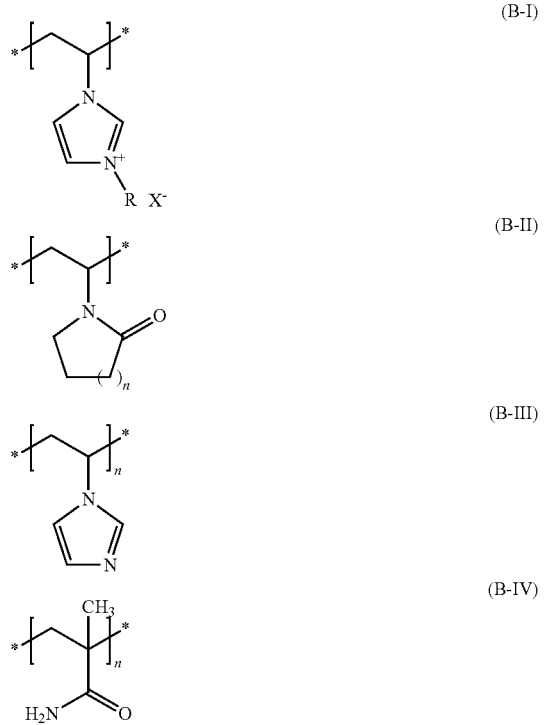

wherein R is a methyl group, X is methosulfate, and n is 1 methylene unit. Here as well, it is particularly preferred if copolymers B3 contain, in addition to polymer units resulting from incorporation into the copolymer of the aforesaid structural units according to formulas (B-I), (B-II), (B-III), and (B-IV), a maximum of 5 wt %, preferably a maximum of 1 wt % polymer units attributable to the incorporation of other monomers. Copolymers B3 are preferably constructed exclusively from structural units of formulas (B-I), (B-II), (B-III), and (B-IV) and can be described by the general formula—

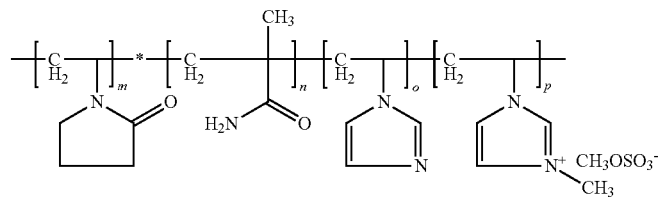

wherein m, n, o, and p vary depending on the molecular weight of the polymer and are not intended to indicate that these are block copolymers. Structural units of formula (B-I), (B-II), (B-III), and (B-IV) can instead be present in statistically distributed fashion in the molecule.

N-methylvinylimidazole/vinylpyrrolidone/vinylimidazole/methacrylamide copolymers of this kind are referred to in INCI nomenclature as Polyquaternium-68, and are obtainable, for example, from BASF under the trade name Luviquat® Supreme.

Very particularly preferred copolymers B3 contain 1 to 12 mol %, preferably 3 to 9 mol %, and in particular 6 mol % structural units according to formula (B-I), and 45 to 65 mol %, preferably 50 to 60 mol %, and in particular 55 mol % structural units according to formula (B-II) where n=1, and 1 to 20 mol %, preferably 5 to 15 mol %, and in particular 10 mol % structural units according to formula (B-III), and 20 to 40 mol %, preferably 25 to 35 mol %, and in particular 29 mol % structural units according to formula (B-IV). Particularly preferred agents contain a copolymer B3 having molecular weights within a specific range. Preferred in this context are agents wherein copolymer B3 has a molecular weight from 100 to 500 kDa, preferably from 150 to 400 kDa, more preferably from 250 to 350 kDa, and in particular from 290 to 310 kDa.

Regardless of whether only one copolymer B or multiple copolymers C are used, and regardless of the choice of the specific copolymer B, agents according to the present invention in which the total quantity of copolymers B, based on total weight of the ready-to-use agent, is 0.05 to 5 wt %, preferably 0.1 to 4 wt %, and in particular 0.25 to 3 wt %, are preferred.

Regardless of whether only one copolymer B or multiple copolymers B are used, and regardless of the choice of the specific copolymer B, agents according to the present invention wherein the total amount of copolymers B, based on total weight of the ready-to-use agent, is 0.05 to 5 wt %, preferably 0.1 to 4 wt %, and in particular 0.25 to 3 wt %, are preferred.

In addition to or instead of the film-forming copolymers B, agents according to the present invention can contain further film-forming polymers C from the group of the acrylate polymers, that is, polymers having at least one monomer unit from the group of acrylic acid and/or methacrylic acid and/or esters thereof. Preferred agents contain at least one acrylate polymer C chosen from c1) polyacrylic acid and/or c2) copolymers of methacrylic acid with acrylamidopropanesulfonic acid and/or c3) copolymers of acrylic acid with methacrylic acid and acrylic acid esters and/or c4) copolymers of acrylic acid with methacrylic acid with acrylic acid esters and methacrylic acid esters and/or c5) copolymers of acrylic acid esters with methacrylic acid.

For example, agents according to the present invention having polyacrylic acid as polymer C are preferred. These have structural units of the formula—

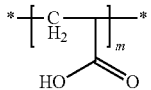

wherein m varies depending on the molecular weight.

Particularly preferred agents according to the present invention contain, as polymer c1, polyacrylic acids having a molecular weight from 10 to 250 kDa, preferably from 25 to 200 kDa, more preferably from 50 to 150 kDa, and in particular from 70 to 100 kDa.

Copolymers c1 are preferably used within specific quantitative ranges. Preferred in this context are agents having, based on total weight of the ready-to-use agent, 0.05 to 5 wt %, preferably 0.1 to 4 wt %, and in particular 0.25 to 3 wt % copolymer(s) c1.

In addition to or instead of polymer(s) c1, agents according to the present invention can also contain polymers c2 from the group of copolymers of methacrylic acid with acrylamidopropanesulfonic acid. These can be described by the general formula—

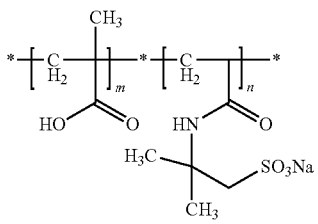

wherein m and n vary depending on the molecular weight of the polymer and are not intended to indicate that these are block copolymers. Structural units can instead be present in statistically distributed fashion in the molecule.

Particularly preferred agents according to the present invention contain, as copolymer c2, copolymers of methacrylic acid with acrylamidopropanesulfonic acid having a molecular weight from 100 to 2500 kDa, preferably from 250 to 2000 kDa, more preferably from 500 to 1750 kDa, and in particular from 800 to 1500 kDa.

Copolymers c2 are preferably used within specific quantitative ranges. Preferred in this context are agents having, based on total weight of the ready-to-use agent, 0.05 to 5 wt %, preferably 0.1 to 4 wt %, and in particular 0.25 to 3 wt % copolymer(s) c2. Copolymers of methacrylic acid and acrylamidopropanesulfonic acid are obtainable, for example, under the trade name Fixomer® A-30 (Nalco).

In addition to or instead of polymer(s) c1 and/or copolymer(s) c2, agents according to the present invention can also contain polymers c3 from the group of copolymers of acrylic acid with methacrylic acid and acrylic acid esters.

These can be described by the general formula—

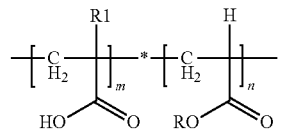

wherein m and n vary depending on the molecular weight of the polymer and are not intended to indicate that these are block copolymers. Structural units can instead be present in statistically distributed fashion in the molecule. R1 is —H or —CH$_3$.

Particularly preferred agents according to the present invention contain, as copolymer c3, copolymers of acrylic acid with methacrylic acid and acrylic acid esters having a molecular Weight from 50 to 500 kDa, preferably from 100 to 400 kDa, more preferably from 150 to 300 kDa, and in particular from 200 to 250 kDa.

Copolymers c3 are preferably used within specific quantity ranges. Preferred in this context are agents having, based on total weight of the ready-to-use agent, 0.05 to 5 wt %, preferably 0.1 to 4 wt %, and in particular 0.25 to 3 wt % copolymer(s) c3. A very particularly preferred copolymer c3 is referred to in INCI nomenclature as Acrylates Copolymer, commercially available, for example, under the tradename Aculyn® 33A (Rohm & Haas).

In addition to or instead of polymer(s) c1 and/or copolymer(s) c2 and/or copolymer(s) c3, agents according to the present invention can also contain polymers c4 from the group of copolymers of acrylic acid with methacrylic acid and ethoxylated acrylic acid esters and ethoxylated methacrylic acid esters.

These can be described by the general formula—

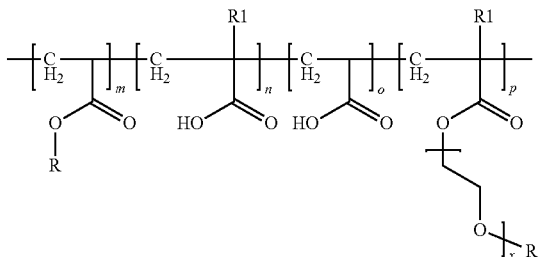

wherein m, n, o and p vary depending on the molecular weight of the polymer and are not intended to indicate that these are block copolymers. Structural units can instead be present in statistically distributed fashion in the molecule. R1 is a methyl group, R is a hydrocarbon having one to 22 carbon atoms, and x is 1 to 50.

Particularly preferred agents according to the present invention contain, as copolymer c4, copolymers of acrylic acid with methacrylic acid and ethoxylated acrylic acid esters and ethoxylated methacrylic acid esters, having a molecular weight from 100 to 500 kDa, preferably from 150 to 400 kDa, more preferably from 200 to 300 kDa, and in particular from 225 to 275 kDa.

Copolymers c4 are preferably used within specific quantity ranges. Preferred in this context are agents having, based on total weight of the ready-to-use agent, 0.05 to 5 wt %, preferably 0.1 to 4 wt %, and in particular 0.25 to 3 wt % copolymer(s) c4.

Particularly preferred copolymers c4 have 20 to 30 EO units (x=20, 21, 22, 23, 24, 25, 26, 27, 28, 29, 30) and possess a stearyl residue or behenyl residue as residue R. A very particularly preferred copolymer c4 has 25 EO units, is esterified with behenyl alcohol, and is referred to in INCI nomenclature as Acrylates/Beheneth-25 Methacrylate Copolymer, commercially available, for example, under the tradename Aculyn® 28 (Rohm & Haas).

In addition to or instead of polymer(s) c1 and/or copolymer(s) c2 and/or copolymer(s) c3 and/or copolymer(s) c4, agents according to the present invention can also contain polymers c5 from the group of copolymers of acrylic acid esters with methacrylic acid. Preferred acrylic acid esters are methyl acrylate and ethyl acrylate, the latter being particularly preferred. Particularly preferred agents according to the present invention contain, as copolymer c5, copolymers of acrylic acid esters with methacrylic acid having a molecular weight from 100 to 500 kDa, preferably from 150 to 400 kDa, more preferably from 200 to 300 kDa, and in particular from 225 to 275 kDa.

Copolymers c5 are preferably used within specific quantity ranges. Preferred in this context are agents having, based on total weight of the ready-to-use agent, 0.05 to 5 wt %, preferably 0.1 to 4 wt %, and in particular 0.25 to 3 wt % copolymer(s) c5. A very particularly preferred copolymer c5 derives from polymerization of methacrylic acid with ethyl acrylate, and is referred to in INCI nomenclature as Acrylates Copolymer, commercially available, for example, under the tradename Luviflex® Soft (BASF).

Very particularly preferred agents according to the present invention therefore contain a copolymer D made of methacrylic acid and ethyl acrylate.

Copolymers D that are used contain preferably 10 to 80 mol %, more preferably 20 to 70 mol %, even more preferably 30 to 60 mol %, and in particular 40 to 50 mol % methacrylic acid, and 20 to 90 mol %, preferably 30 to 80 mol %, more preferably 40 to 70 mol %, and in particular 50 to 60 mol % ethyl acrylate.

Even more preferred are agents in which copolymer D has a molecular weight from 100 to 800 kDa, preferably from 200 to 700 kDa, more preferably from 300 to 600 kDa, and in particular from 450 to 550 kDa. Particularly preferably, the agent contains the copolymer marketed by BASF AG under the tradename Luviflex® Soft (INCI name: Acrylates Copolymer).

Regardless of which copolymer(s) C and D is/are used, preferred agents according to the present invention have a total amount of copolymers C and D, based on total weight of the ready-to-use agent, is 0.05 to 5 wt %, preferably 0.1 to 4 wt %, and in particular 0.25 to 3 wt %.

The present invention is not restricted regarding selection of the additionally usable copolymers B and C or D (D is a preferred polymer c5). It is possible to use only a single polymer in each case, or multiple polymers in each case, from the individual classes described above. Particularly preferred agents contain, in addition to copolymer A that is obligatorily used according to the present invention and the at least one silicone that is obligatorily present.

Agents according to the present invention wherein the weight ratio of polymer(s) B to polymer(s) C is equal to 10:1 to 1:10, preferably 8:1 to 1:8, more preferably 5:1 to 1:5, and in particular 4:1 to 1:4, are preferred. Regardless of the nature and weight ratio to one another of the polymers, agents according to the present invention wherein the total polymer content (B+C+D) of the agents is equal to 1 to 15 wt %, preferably 2.5 to 12.5 wt %, more preferably 4 to 10 wt %, and in particular 5 to 8 wt %, are furthermore preferred.

In addition to or instead of the film-forming copolymers B and/or C and/or D, agents according to the present invention can contain further film-forming polymers E from the group of acrylate polymers, that is, polymers having at least one monomer unit from acrylic acid and/or methacrylic acid and/or esters thereof. Preferred agents according to the present invention contain at least one copolymer E formed from at least one monomer e1 chosen from acrylic acid and/or methacrylic acid, and at least one monomer e2 chosen from acrylamide and/or methacrylamide, and at least one monomer e3 chosen from N-substituted acrylamides and/or methacrylamides.

This copolymer E contains at least one monomer e1 chosen from acrylic acid and/or methacrylic acid, and at least one monomer e2 chosen from acrylamide and/or methacrylamide, and at least one monomer e3 chosen from N-substituted acrylamides and/or methacrylamides, and can moreover comprise further structural units that are polymerized in during polymerization by addition of corresponding monomers.

Particularly preferred copolymers A are copolymers of acrylic acid and acrylamide and N-substituted acrylamides; acrylic acid and methacrylamide and N-substituted acrylamides; methacrylic acid and acrylamide and N-substituted acrylamides; methacrylic acid and methacrylamide and N-substituted acrylamides and/or methacrylamides; acrylic acid and acrylamide and N-substituted methacrylamides; acrylic acid and methacrylamide and N-substituted methacrylamides; methacrylic acid and acrylamide and N-substituted methacrylamides; methacrylic acid and methacrylamide and N-substituted methacrylamides. Particularly preferred agents according to the present invention contain, as copolymer E, a copolymer E1 having acrylic acid as monomer e1.

A preferred monomer is acrylamide. Preferred agents according to the present invention contain, as copolymer E, a copolymer E1 that encompasses acrylamide as monomer e2.

N-substitution on the N-substituted acrylamides can be accomplished using simple alkyl groups (preferably methyl, ethyl, n-propyl, isopropyl), but substituted alkyl groups carrying anionic functionalities are particularly preferred. Sulfonate-group-containing substituents are very particularly preferred.

A particularly preferred agent according to the present invention contains, as copolymer E, a copolymer E1 that encompasses acryloyldimethyltaurate as monomer e3. These copolymers E1 can be described by the general formula—

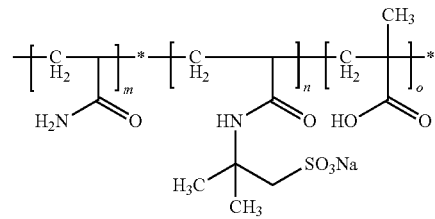

wherein m, n and o vary depending on the molecular weight of the polymer and are not intended to indicate that these are block copolymers. Structural units can instead be present in statistically distributed fashion in the molecule.

Particularly preferred agents according to the present invention are those wherein copolymer E1 has a molecular weight from 50 to 500 kDa, preferably from 100 to 450 kDa, more preferably from 150 to 400 kDa, and in particular from 200 to 300 kDa.

Copolymers E are preferably used within specific quantity ranges. Preferred in this context are agents wherein the total amount of copolymers E, based on total weight of the ready-to-use agent, is 0.05 to 5 wt %, preferably 0.1 to 4 wt %, and in particular 0.25 to 3 wt %. Copolymers of acrylamide with methacrylic acid and acryloyldimethyltaurate are obtainable, for example, under the tradename Acudyne® SCP (Rohm & Haas).

In addition to or instead of the film-forming copolymers B and/or C and/or D and/or E, agents according to the present invention can contain further film-forming polymers F. Preferred agents according to the present invention contain at least one copolymer F chosen from f1) copolymers of vinylpyrrolidone with methacrylamidopropyltrimethylammonium chloride (MAPTAC) and/or f2) copolymers of vinylpyrrolidone with dimethylaminoethyl methacrylate and/or f3) copolymers of vinylpyrrolidone with dimethylaminopropylmethacrylamide and alkyldimethylpropylmethacrylamidoammonium salts. For example, agents having, as polymer F, copolymers of vinylpyrrolidone with methacrylamidopropyltrimethylammonium chloride (MAPTAC) (b1) are preferred.

These can be described by the general formula—

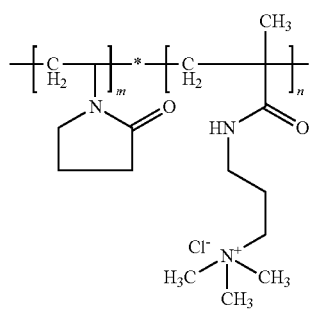

wherein m and n vary depending on the molecular weight of the polymer and are not intended to indicate that these are block copolymers. Structural units can instead be present in statistically distributed fashion in the molecule.

Particularly preferred agents according to the present invention contain, as cationic polymer f1, copolymers of methacrylamidopropyltrimethylammonium chloride (MAPTAC) with vinylpyrrolidone having 40 to 95 mol %, preferably 42.5 to 90 mol %, more preferably 45 to 85 mol %, and in particular 50 to 80 mol % vinylpyrrolidone.

Particularly preferred agents according to the present invention are those wherein copolymers f1 have molecular weights from 10 to 1000 kDa, preferably from 25 to 900 kDa, more preferably from 50 to 800 kDa, and in particular from 100 to 750 kDa.

Copolymers f1 are preferably used within specific quantity ranges. Preferred in this context are agents that contain, based on total weight of the ready-to-use agent, 0.05 to 5 wt %, preferably 0.1 to 4 wt %, and in particular 0.25 to 3 wt % copolymer(s) f1. A very particularly preferred copolymer f1 is referred to in INCI nomenclature as Polyquaternium-28. A polymer of this kind is obtainable, for example, under the tradename Gafquat® HS-100 (ISP).

In addition to or instead of polymer(s) f1, agents according to the present invention can also contain polymers f2 from copolymers of vinylpyrrolidone and dimethylaminoethyl methacrylate.

These can be described by the general formula—

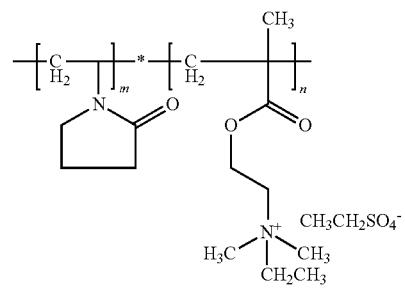

wherein m and n vary depending on the molecular weight of the polymer and are not intended to indicate that these are block copolymers. Structural units can instead be present in statistically distributed fashion in the molecule.

Particularly preferred agents according to the present invention contain, as cationic polymer f, copolymers of vinylpyrrolidone with dimethylaminoethyl methacrylate that contain 40 to 95 mol %, preferably 42.5 to 90 mol %, more preferably 45 to 85 mol %, and in particular 50 to 80 mol % vinylpyrrolidone.

Particularly preferred agents are those wherein copolymers f2 have molecular weights from 100 to 2500 kDa, preferably from 250 to 2000 kDa, more preferably from 500 to 1750 kDa, and in particular from 800 to 1500 kDa.

Copolymers f2 are preferably used within specific quantity ranges. Preferred in this context are agents having, based on total weight of the ready-to-use agent, 0.05 to 5 wt %, preferably 0.1 to 4 wt %, and in particular 0.25 to 3 wt % copolymer(s) f2. A very particularly preferred copolymer f2 is referred to in INCI nomenclature as Polyquaternium-11, commercially available, for example, under the tradename Gafquat® 755 N (ISP).

In addition to or instead of polymer(s) f1 and/or polymer(s) f2, agents according to the present invention can also contain polymers f3 from copolymers of vinylpyrrolidone with dimethylaminopropylmethacrylamide and alkyldimethylpropylmethacrylamidoammonium salts.

These can be described by the general formula—

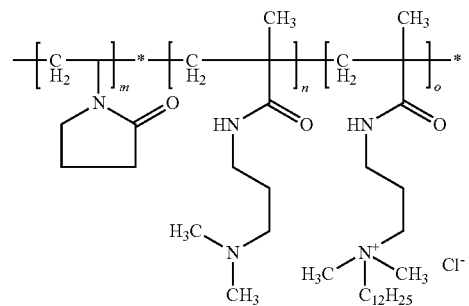

wherein m, n and o vary depending on the molecular weight of the polymer and are not intended to indicate that these are block copolymers. Structural units can instead be present in statistically distributed fashion in the molecule.

Particularly preferred agents contain, as cationic polymer f3, copolymers of vinylpyrrolidone with dimethylaminopropylmethacrylamide and lauryldimethylpropylmethacrylamidoammonium salts.

Particularly preferred agents according to the present invention contain, as cationic copolymer f3, copolymers of vinylpyrrolidone with dimethylaminopropylmethacrylamide and alkyldimethylpropylmethacrylamidoammonium salts having 40 to 95 mol %, preferably 42.5 to 90 mol %, more preferably 45 to 85 mol %, and in particular 50 to 80 mol % vinylpyrrolidone. Very particularly preferred agents according to the present invention are those wherein copolymers f3 have molecular weights from 10 to 1000 kDa, preferably from 25 to 900 kDa, more preferably from 50 to 800 kDa, and in particular from 100 to 750 kDa. Copolymers f3 are preferably used within specific quantity ranges. Preferred are agents having, based on total weight of the ready-to-use agent, 0.05 to 5 wt %, preferably 0.1 to 4 wt %, and in particular 0.25 to 3 wt % copolymer(s) f3. A very particularly preferred copolymer f3 is referred to in INCI nomenclature as Polyquaternium-55, commercially available, for example, under the tradename Styleze® W20 (ISP).

Regardless of the nature and weight ratio to one another of all the polymers present in agents according to the present invention, agents wherein the total polymer content of the agents is equal to 1 to 15 wt %, preferably 2.5 to 12.5 wt %, more preferably 4 to 10 wt %, and in particular 5 to 8 wt %, are furthermore preferred.

Agents according to the present invention contain the ingredients in a cosmetically acceptable carrier.

Preferred cosmetically acceptable carriers are aqueous, alcoholic, or aqueous/alcoholic media having preferably at least 10 wt % water, based on total agent. Alcohols present can be, in particular, lower alcohols having 1 to 4 carbon atoms usually used for cosmetic purposes, for example, ethanol and isopropanol.

Organic solvents or a mixture of solvents having a boiling point under 400° C. can be used as additional co-solvents in an amount from 0.1 to 15 weight percent, preferably 1 to 10 weight percent, based on total agent. Unbranched or branched hydrocarbons such as pentane, hexane, isopentane, and cyclic hydrocarbons such as cyclopentane and cyclohexane, are particularly suitable as additional co-solvents. Further particularly preferred water-soluble solvents are glycerol, ethylene glycol, butylene glycol, and propylene glycol, in an amount of up to 30 wt % based on total agent.

The agents preferably have a pH from 2 to 11. Particularly preferably, the pH range is from 4 to 9. Unless otherwise noted, the indications regarding pH refer, for purposes of this document, to the pH at 25° C.

Agents according to the present invention can also contain adjuvants and additives typically added to the respective cosmetic agents.

Care-providing substances may be mentioned in particular as suitable adjuvants and additives. These are utilized in both skin and hair treatment agents, and, with suitable selection of the care-providing substance, can be incorporated, for example, into creams, shampoos, hair rinses, hair therapies, gels, pump and aerosol sprays, and foam products.

An agent according to the present invention can contain as a care-providing substance, for example, at least one protein hydrolysate and/or one of its derivatives.

Protein hydrolysates are product mixtures obtained by the acid-, base-, or enzyme-catalyzed breakdown of proteins. The molecular weight of protein hydrolysates usable according to the present invention is from about 75 (the molecular weight of glycine) to about 200,000; the molecular weight is preferably 75 to 50,000 Dalton, and very particularly preferably 75 to 20,000 Dalton.

According to the present invention, protein hydrolysates of both plant and animal origin, or of marine or synthetic origin, can be used. Animal protein hydrolysates include hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm), and Kerasol® (Croda). The use of silk protein hydrolysates is of particular interest. Protein hydrolysates are present in agents according to the present invention, for example, in concentrations from 0.01 wt % to 20 wt %, preferably from 0.05 wt % to 15 wt %, and very particularly in amounts from 0.05 wt % to 5 wt %, based on total application preparation.

Cationic surfactants are also suitable as a care-providing substance of a different class of compound. Cationic surfactants of the quaternary ammonium compound, esterquat, and amidoamine types are preferred according to the present invention. Preferred quaternary ammonium compounds include ammonium halides, in particular chlorides and bromides such as alkyltrimethylammonium chlorides, dialkyldimethylammonium chlorides, and trialkylmethylammonium chlorides (e.g., cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride), as well as the imidazolium compounds known by the INCI names Quaternium-27 and Quaternium-83. Long alkyl chains of the aforementioned surfactants preferably have 10 to 18 carbon atoms. Esterquats are known substances having both at least one ester function and at least one quaternary ammonium group as a structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed, for example, under the trademarks Stepantex®, Dehyquart®, and Armocare®. Examples of such esterquats are the products Armocare® VGH-70—an N,N-bis(2-palmitoyloxyethyl)dimethylammonium chloride—as well as Dehyquart® F-75, Dehyquart® C-4046, Dehyquart® L-80, and Dehyquart® AU-35. The alkylamidoamines are usually produced by amidation of natural or synthetic fatty acids and fatty acid cuts with dialkylaminoamines. One compound from this group of substances that is particularly suitable is the stearamidopropyldimethylamine available commercially under the designation Tegoamid® S18.

Cationic surfactants are preferably present in agents according to the present invention in amounts from 0.05 to 10 wt %, based on total application preparation. Quantities from 0.1 to 5 wt % are particularly preferred.

Care-providing polymers are also suitable as a care-providing substance. Some care-providing polymers also exhibit film-forming and/or setting properties, and can therefore also be recited when listing suitable film-forming and/or setting polymers.

A first group of care-providing polymers is the cationic polymers. "Cationic polymers" are to be understood as polymers having in the main chain and/or side chain a group that can be "temporarily" or "permanently" cationic. According to the present invention, those polymers having a cationic group regardless of the pH of the agent are referred to as "permanently cationic." These are, as a rule, polymers having a quaternary nitrogen atom, for example, in the form of an ammonium group. Preferred cationic groups are quaternary ammonium groups. In particular, those polymers wherein the quaternary ammonium group is bound via a $C_{1-4}$ hydrocarbon group to a main polymer chain made up of acrylic acid, methacrylic acid, or derivatives thereof, have proven to be particularly suitable.

Homopolymers of the general formula (G1-I)—

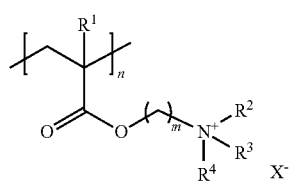

(G1-I)

wherein $R^1$=—H or —$CH_3$, $R^2$, $R^3$ and $R^4$ are chosen, mutually independently, from $C_{1-4}$ alkyl, alkenyl, or hydroxyalkyl groups, m=1, 2, 3 or 4, n is a natural number, and r is a physiologically acceptable organic or inorganic anion, as well as copolymers made up substantially of the monomer units presented in formula (G1-I) as well as nonionogenic monomer units, are particularly preferred cationic polymers. These polymers (those for which at least one of the following conditions applies) are preferred according to the present invention: $R^1$ is a methyl group, $R^2$, $R^3$ and $R^4$ are methyl groups, m is 2.

Possibilities as physiologically acceptable counterions X⁻ include halide ions, sulfate ions, phosphate ions, methosulfate ions, and organic ions such as lactate, citrate, tartrate, and acetate ions. Halide ions, in particular chloride, are preferred.

A particularly suitable homopolymer is poly(methacryloyloxyethyltrimethylammonium chloride) (crosslinked, if desired) having the INCI name Polyquaternium-37. Crosslinking can be accomplished, if desired, with the aid of polyolefinically unsaturated compounds such as divinylbenzene, tetraallyloxyethane, methylene bisacrylamide, diallyl ether, polyallylpolyglyceryl ether, or allyl ethers of sugars or sugar derivatives such as erythritol, pentaerythritol, arabitol, mannitol, sorbitol, sucrose, or glucose. Methylene bisacrylamide is a preferred cross-linking agent.

The homopolymer is preferably used in the form of a nonaqueous polymer dispersion comprising a polymer proportion not less than 30 wt %. Such polymer dispersions are commercially available under the designations Salcare® SC 95 (approx. 50% polymer proportion, further components: mineral oil (INCI name: Mineral Oil) and tridecylpolyoxypropylenepolyoxyethylene ether (INCI name: PPG-1-Trideceth-6)), and Salcare® SC 96 (approx. 50% polymer proportion, further components: mixture of diesters of propylene glycol with a mixture of caprylic and capric acid (INCI name: Propylene Glycol Dicaprylate/Dicaprate) and tridecylpolyoxypropylenepolyoxyethylene ether (INCI name: PPG-1-Trideceth-6)).

Copolymers having monomer units according to formula (G1-I) preferably contain acrylamide, methacrylamide, acrylic acid $C_{1-4}$ alkyl esters, and methacrylic acid $C_{1-4}$ alkyl esters as nonionogenic monomer units. Of these nonionogenic monomers, acrylamide is particularly preferred. These copolymers as well (as in the case of the homopolymers described above) can be crosslinked. A copolymer preferred according to the present invention is the crosslinked copolymer of acrylamide and methacryloyloxyethyltrimethylammonium chloride. Such copolymers, in which the monomers are present at a weight ratio of approximately 20:80, are commercially obtainable as an approximately 50% nonaqueous polymer dispersion under the designation Salcare® SC 92.

Additional preferred cationic polymers include—
quaternized cellulose derivatives such as those obtainable commercially under the tradenames Celquat® and Polymer JR®. The compounds Celquat® H 100, Celquat® L 200, and Polymer JR® 400 are preferred quaternized cellulose derivatives;

cationic alkyl polyglycosides according to DE Patent 44 13 686;

cationized honey, for example the commercial product Honeyquat® 50;

cationic guar derivatives such as, in particular, the products marketed under the trade names Cosmedia® Guar and Jaguar®;

polysiloxanes having quaternary groups such as the commercially obtainable products Q2-7224 (manufacturer: Dow Corning; a stabilized trimethylsilylamodimethicone), Dow Corning® 929 Emulsion (containing a hydroxylamino-modified silicone that is also referred to as Amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80);

polymeric dimethyldiallylammonium salts and copolymers thereof with esters and amides of acrylic acid and methacrylic acid. Products commercially available under the tradenames Merquat® 100 (poly(dimethyldiallylammonium chloride)) and Merquat® 550 (dimethyldiallylammonium chloride/acrylamide copolymer) are examples of such cationic polymers;

quaternized poly(vinylalcohol); and polymers known under the designations Polyquaternium-2, Polyquaternium-17, Polyquaternium-18, and Polyquaternium-27, having quaternary nitrogen atoms in the main polymer chain.

Additional cationic polymers usable according to the present invention are the so-called "temporarily cationic" polymers. These polymers usually contain an amino group that is present at certain pH values as a quaternary ammonium group and therefore are cationic. Chitosan and its derivatives, such as those commercially available under the tradenames Hydagen® CMF, Hydagen® HCMF, Kytamer® PC, and Chitolam® NB/101, are, for example, preferred.

Agents according to the present invention contain care-providing cationic and/or amphoteric polymers preferably in an amount from 0.01 to 5 wt %, particularly from 0.1 to 2 wt %, based on total application preparation.

Further preferred agents according to the present invention additionally contain care-providing substance(s), based on their weight, in amounts from 0.001 to 10 wt %, preferably 0.005 to 7.5 wt %, particularly preferably 0.01 to 5 wt %, and in particular 0.05 to 2.5 wt %, preferred care-providing substance(s) chosen from L-carnitine and/or salts thereof; panthenol and/or pantothenic acid; 2-furanones and/or derivatives thereof, in particular pantolactone; taurine and/or salts thereof; niacinamide; ubiquinone; ectoin; allantoin.

L-carnitine (IUPAC name: (R)-(3-carboxy-2-hydroxypropyl)-N,N,N-trimethylammonium hydroxide) is a naturally occurring vitamin-like substance. L-carnitine derivatives preferred according to the present invention are chosen in particular from acetyl-L-carnitine, L-carnitine fumarate, L-carnitine citrate, lauroyl-L-carnitine, and particularly preferably L-carnitine tartrate. The aforesaid L-carnitine compounds are obtainable, for example, from Lonza GmbH (Wuppertal, Germany). Agents preferred according to the present invention contain, based on their weight, 0.001 to 10 wt %, preferably 0.005 to 7.5 wt %, particularly preferably 0.01 to 5 wt %, and in particular 0.05 to 2.5 wt % L-carnitine or L-carnitine derivatives, chosen from acetyl-L-carnitine, L-carnitine fumarate, L-carnitine citrate, lauroyl-L-carnitine, and in particular L-carnitine tartrate.

Panthenol (IUPAC-Name: (+)-(R)-2,4-dihydroxy-N-(3-hydroxypropyl)-3,3-dimethylbutyramide) is converted in the body to pantothenic acid. Pantothenic acid is a vitamin from the group of the B vitamins (vitamin B5). Preferred agents contain, based on total weight, 0.01 to 5 wt %, preferably 0.05 to 2.5 wt %, particularly preferably 0.1 to 1.5 wt %, and in particular 0.25 to 1 wt % panthenol ((±)-2,4-dihydroxy-N-(3-hydroxypropyl)-3,3-dimethylbutyramide).

A further care enhancer that is preferred for use, which possesses activating properties, is taurine. Agents preferred according to the present invention contain, based on their weight, 0.01 to 15 wt %, by preference 0.025 to 12.5 wt %, particularly preferably 0.05 to 10 wt %, more preferably 0.1 to 7.5 wt %, and in particular 0.5 to 5 wt % taurine (2-aminoethanesulfonic acid).

A further preferred group of care enhancers in agents according to the present invention is vitamins, provitamins, or vitamin precursors. These are described below.

In summary, agents having, based on their weight, 0.1 to 5 wt %, preferably 0.2 to 4 wt %, more preferably 0.25 to 3.5 wt %, even more preferably 0.5 to 3 wt %, and in particular 0.5 to 2.5 wt % vitamins and/or provitamins and/or vitamin precursors that preferably are assigned to the groups A, B, C, E, F, and H, such that preferred agents contain-2,4-dihydroxy-N-(3-hydroxypropyl)-3,3-dimethylbutyramide (provitamin $B_5$) and/or pantothenic acid (vitamin $B_3$, vitamin $B_5$) and/or niacin, niacinamide or nicotinamide (vitamin $B_3$) and/or L-ascorbic acid (vitamin C) and/or thiamin (vitamin $B_1$) and/or riboflavin (vitamin $B_2$, vitamin G) and/or biotin (vitamin $B_7$, vitamin H) and/or folic acid (vitamin $B_9$, vitamin $B_c$ or vitamin M) and/or vitamin $B_6$ and/or vitamin $B_{12}$, are preferred.

It has been found that certain quinones possess a particular suitability as a care enhancer. Particularly preferred agents according to the present invention contain as a care-providing substance, based on their weight, 0.0001 to 5 wt %, preferably 0.001 to 0.5 wt %, and particularly preferably 0.005 to 0.1 wt % of at least one ubiquinone and/or at least one ubiquinol and/or at least one derivative of said substances. Preferred agents contain a ubiquinone of formula (Ubi)

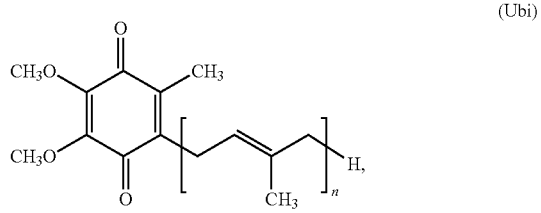

(Ubi)

wherein n is 6, 7, 8, 9, or 10, particularly preferably 10 (coenzyme Q10).

As a further care enhancer, the agents can contain ectoin. Ectoin ((4S)-2-methyl-1,4,5,6-tetrahydropyrimidine-4-carboxylic acid) is a natural substance belonging to the group of the compatible solutes.

As a further constituent, agents according to the present invention can contain at least one carbohydrate from monosaccharides, disaccharides, and/or oligosaccharides. Hair treatment agents preferred according to the present invention contain as a care-providing substance, based on their weight, 0.01 to 5 wt %, preferably 0.05 to 4.5 wt %, particularly preferably 0.1 to 4 wt %, more preferably 0.5 to 3.5 wt %, and in particular 0.75 to 2.5 wt % carbohydrate(s) chosen from monosaccharides, disaccharides, and/or oligosaccharides, preferred carbohydrates including monosaccharides, particularly D-ribose and/or D-xylose and/or L-arabinose and/or D-glucose and/or D-mannose and/or D-galactose and/or D-fructose and/or sorbose and/or L-fucose and/or L-rhamnose, disaccharides, particularly sucrose and/or maltose and/or lactose and/or trehalose and/or cellobiose and/or gentobiose and/or isomaltose.

In a further preferred embodiment, agents according to the present invention can contain emulsifiers (F). Emulsifiers cause at the phase interface the formation of water- or oil-stable adsorption layers that prevent the dispersed droplets from coalescing, thereby stabilizing the emulsion. Emulsifiers are therefore, like surfactants, constructed from a hydrophobic and a hydrophilic molecule part. Hydrophilic emulsifiers preferentially form o/w emulsions, and hydrophobic emulsifiers preferentially form w/o emulsions. An "emulsion" is to be understood as a droplet-like distribution (dispersion) of one liquid in another liquid, with the expenditure of energy to create stabilizing phase interfaces by means of surfactants. Selection of these emulsifying surfactants or emulsifiers is based on the substances dispersed and the respective external phase, and on the fineness of the emulsion particles. Emulsifiers usable according to the present invention include:

addition products of 4 to 30 mol ethylene oxide and/or 0 to 5 mol propylene oxide with linear fatty alcohols having 8 to 22 carbon atoms, with fatty acids having 12 to 22 carbon atoms, and with alkylphenols having 8 to 15 carbon atoms in the alkyl group;

$C_{12}$ to $C_{22}$ fatty acid mono- and diesters of addition products of 1 to 30 mol ethylene oxide with polyols having 3 to 6 carbon atoms, in particular with glycerol;

addition products of ethylene oxide and polyglycerol with methyl glucoside fatty acid esters, fatty acid alkanolamides, and fatty acid glucamides;

$C_8$ to $C_{22}$ alkyl mono- and oligoglycosides and ethoxylated analogs thereof, degrees of oligomerization from 1.1 to 5, particularly 1.2 to 2.0, and glucose as the sugar component, being preferred;

mixtures of alkyl(oligo)glucosides and fatty alcohols, for example, the commercially available product Montanov® 68;

addition products of 5 to 60 mol ethylene oxide with castor oil and hardened castor oil;

partial esters of polyols having 3 to 6 carbon atoms with saturated fatty acids having 8 to 22 carbon atoms;

Sterols. "Sterols" are understood as a group of steroids that carry a hydroxyl group on the third carbon atom of the steroid structure and are isolated both from animal tissue (zoosterols) and from vegetable fats (phytosterols). Examples of zoosterols are cholesterol and lanosterol. Examples of suitable phytosterols are ergosterol, stigmasterol, and sitosterol. Sterols called "mycosterols" are also isolated from fungi and yeasts.

Phospholipids. These are understood as principally the glucose phospholipids, obtainable, for example, as lecithins or phosphatidylcholines from, for example, egg yolk or plant seeds (e.g., soybeans).

fatty acid esters of sugars and sugar alcohols such as sorbitol;

polyglycerols and polyglycerol derivatives such as polyglycerol poly-12-hydroxystearate (commercial product Dehymuls® PGPH).

linear and branched fatty acids having 8 to 30 carbon atoms, and the Na, K, ammonium, Ca, Mg, and Zn salts thereof.

Agents according to the present invention contain emulsifiers preferably in amounts from 0.1 to 25 wt %, particularly 0.5 to 15 wt %, based on total entire agent. Compositions according to the present invention can preferably contain at least one nonionogenic emulsifier having an HLB value from 8 to 18. Nonionogenic emulsifiers having an HLB value from 10 to 15 can be particularly preferred according to the present invention.

Depending on the nature of the agent according to the present invention, it may be necessary for it to contain at least one surfactant. This applies in particular to skin cleaning agents and shampoos. Other agents as well, however, such as hair rinses, hair therapies, and certain styling agents, in particular styling foams, can contain surfactants.

Cationic surfactants, for example, those already described above as suitable care-providing substances, can be used. The statements made above apply correspondingly with regard to the preferred cationic surfactants and quantities used.

In addition to or instead of the cationic surfactants, the agents can contain further surfactants or emulsifiers, both anionic as well as ampholytic and nonionic surfactants, and all types of known emulsifiers being suitable in principle. The group of ampholytic or also amphoteric surfactants encompasses zwitterionic surfactants and ampholytes. The surfactants can already have an emulsifying effect.

All anionic surface-active substances suitable for use on the human body are, in principle, appropriate as anionic surfactants. These have an anionic group imparting water solubility, for example, a carboxylate, sulfate, sulfonate, or phosphate group, and a lipophilic alkyl group having approximately 8 to 30 carbon atoms. Glycol or polyglycol ether groups, ester, ether, and amide groups, and hydroxyl groups can additionally be contained in the molecule. Examples of suitable anionic surfactants include, in each case in the form of the sodium, potassium, and ammonium and mono-, di-, and trialkanolammonium salts having 2 to 4 carbon atoms in the alkanol group:

linear and branched fatty acids having 8 to 30 carbon atoms (soaps);
ethercarboxylic acids of the formula R—O—(CH$_2$—CH$_2$O)$_x$—CH$_2$—COOH, in which R is a linear alkyl group having 8 to 30 carbon atoms and x=0 or is 1 to 16;
acyl sarcosides having 8 to 24 carbon atoms in the acyl group;
acyl taurides having 8 to 24 carbon atoms in the acyl group;
acyl isethionates having 8 to 24 carbon atoms in the acyl group;
sulfosuccinic acid mono- and dialkyl esters having 8 to 24 carbon atoms in the alkyl group, and sulfosuccinic acid monoalkylpolyoxyethyl esters having 8 to 24 carbon atoms in the alkyl group and 1 to 6 oxyethyl groups;
linear alkanesulfonates having 8 to 24 carbon atoms;
linear alpha-olefinsulfonates having 8 to 24 carbon atoms;
alpha-sulfo fatty acid methyl esters of fatty acids having 8 to 30 carbon atoms;
alkyl sulfates and alkyl polyglycol ether sulfates of the formula R—O—(CH$_2$—CH$_2$—O)$_x$—OSO$_3$H, wherein R is a preferably linear alkyl group having 8 to 30 carbon atoms and x=0 or is 1 to 12;
mixtures of surface-active hydroxysulfonates;
sulfated hydroxyalkylpolyethylene and/or hydroxyalkylenepropylene glycol ethers;
sulfonates of unsaturated fatty acids having 8 to 24 carbon atoms and 1 to 6 double bonds;
esters of tartaric acid and citric acid with alcohols, representing addition products of approximately 2 to 15 molecules of ethylene oxide and/or propylene oxide with fatty alcohols having 8 to 22 carbon atoms;
alkyl and/or alkenyl ether phosphates;
sulfated fatty acid alkylene glycol esters of formula (E1-II):

$$R^7CO(AlkO)_nSO_3M \qquad (E1\text{-}II)$$

wherein $R^7CO$ is a linear or branched, aliphatic, saturated and/or unsaturated acyl residue having 6 to 22 carbon atoms, Alk is CH$_2$CH$_2$, CHCH$_3$CH$_2$, and/or CH$_2$CHCH$_3$, n is a number from 0.5 to 5, and M is a cation, such as those described in German Patent Application No. 197 36 906;
amide ethercarboxylic acids;
condensation products of C$_8$ to C$_{30}$ fatty alcohols with protein hydrolysates and/or amino acids and derivatives thereof, known to one skilled in the art as protein fatty acid condensates, such as Lamepon® grades, Gluadin® grades, Hostapon® KCG, or the Amisoft® grades.

Preferred anionic surfactants are alkyl sulfates, alkyl polyglycol ether sulfates, and ethercarboxylic acids having 10 to 18 carbon atoms in the alkyl group and up to 12 glycol ether groups in the molecule, sulfosuccinic acid mono- and dialkyl esters having 8 to 18 carbon atoms in the alkyl group, and sulfosuccinic acid monoalkylpolyoxyethyl esters having 8 to 18 carbon atoms in the alkyl group and 1 to 6 oxyethyl groups, monoglycerol disulfates, alkyl and alkenyl ether phosphates, and protein fatty acid condensates.

"Zwitterionic surfactants" refers to those surface-active compounds that contain in the molecule at least one quaternary ammonium group and at least one —COO$^{(-)}$ or —SO$_3^{(-)}$ group. Particularly suitable zwitterionic surfactants are the betaines, such as N-alkyl-N,N-dimethylammonium glycinates, for example, cocalkyldimethylammonium glycinate, N-acylaminopropyl-N,N-dimethylammonium glycinates, for example, cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

"Ampholytes" are understood to be those surface-active compounds having in the molecule, in addition to a C$_8$ to C$_{24}$ alkyl or acyl group, at least one free amino group and at least one —COOH or —SO$_3$H group, and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. Particularly preferred ampholytes are N-cocalkylaminopropionate, cocacylaminoethylaminopropionate, and C$_{12-18}$ acyl sarcosine.

Nonionic surfactants contain as a hydrophilic group, for example, a polyol group, a polyalkylene glycol ether group, or a combination of a polyol and polyglycol ether group. Such compounds include— addition products of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group;
addition products, end-capped with a methyl or C$_2$ to C$_6$ alkyl group, of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as, for example, the grades obtainable under the marketing designations Dehydrol® LS, Dehydrol® LT (Cognis);
C$_{12}$ to C$_{30}$ fatty acid mono- and diesters of addition products of 1 to 30 mol ethylene oxide with glycerol;

addition products of 5 to 60 mol ethylene oxide with castor oil and hardened castor oil;

polyol fatty acid esters such as, for example, the commercial product Hydagen® HSP (Cognis), or Sovermol grades (Cognis);

alkoxylated triglycerides;

alkoxylated fatty acid alkyl esters of formula (E4-I):

$$R^1CO\text{—}(OCH_2CHR^2)_wOR^3 \quad (E4\text{-}I),$$

wherein $R^1CO$ is a linear or branched, saturated and/or unsaturated acyl residue having 6 to 22 carbon atoms, $R^2$ is hydrogen or methyl, $R^3$ is linear or branched alkyl residues having 1 to 4 carbon atoms, and w is a number from 1 to 20;

amine oxides;

sorbitan fatty acid esters and addition products of ethylene oxide with sorbitan fatty acid esters, for example the polysorbates;

sugar fatty acid esters and addition products of ethylene oxide with sugar fatty acid esters;

addition products of ethylene oxide with fatty acid alkanolamides and fatty amines;

sugar surfactants of the alkyl and alkenyl oligoglycoside types, according to formula (E4-II)

$$R^4O\text{-}[G]_p \quad (E4\text{-}II)$$

wherein $R^4$ is an alkyl or alkenyl residue having 4 to 22 carbon atoms, G is a sugar residue having 5 or 6 carbon atoms, and p is a number from 1 to 10. They can be obtained in accordance with the relevant methods of preparative organic chemistry. The preferred alkyl or alkenyl oligoglycosides are thus alkyl and/or alkenyl oligoglucosides. The index number p in the general formula (E4-II) indicates the degree of oligomerization (DP), i.e., the distribution of mono- and oligoglycosides, and is a number between 1 and 10. The alkyl or alkenyl residue $R^4$ can be derived from primary alcohols having 4 to 11, preferably 8 to 10 carbon atoms. Alkyl oligoglucosides based on hardened $C_{12/14}$ cocalcohol having a DP of 1 to 3 are preferred.

The alkylene oxide addition products with saturated linear fatty alcohols and fatty acids, having respectively 2 to 30 mol ethylene oxide per mol fatty alcohol or fatty acid, have proven to be further preferred nonionic surfactants. Preparations having outstanding properties are likewise obtained if they contain, as nonionic surfactants, fatty acid esters of ethoxylated glycerol. These compounds have the following parameters: The alkyl residue R contains 6 to 22 carbon atoms and can be both linear and branched. Primary linear aliphatic residues, and those methyl-branched in the 2-position, are preferred. Such alkyl residues include 1-octyl, 1-decyl, 1-lauryl, 1-myristyl, 1-cetyl, and 1-stearyl. 1-Octyl, 1-decyl, 1-lauryl, and 1-myristyl are particularly preferred. When so-called "oxo alcohols" are used as the initial materials, compounds having an odd number of carbon atoms in the alkyl chain predominate.

The compounds having alkyl groups used as surfactants can in each case be uniform substances. It is generally preferred, however, to proceed from natural vegetable or animal raw materials when producing these substances, so that substance mixtures having different alkyl chain lengths, dependent on the particular material, are obtained.

These further surfactants are used as a rule in amounts from 0.1 to 45 wt %, preferably 0.5 to 30 wt %, and very particularly preferably from 0.5 to 25 wt %, based on the respective entire composition. The amount used depends substantially on the purpose being fulfilled by the agent according to the present invention. In the case of a shampoo or another cleaning agent, surfactant quantities above 45 wt % are also usual.

Agents according to the present invention can be formulated in any form usual for cosmetic agents, for example, in the form of solutions that can be applied onto the skin or hair as a face or hair lotion or as a pump or aerosol spray, in the form of creams, emulsions, waxes, gels, or also surfactant-containing foaming solutions or other preparations that are suitable for application to the skin or hair.

Agents according to the present invention are, however, preferably agents for the temporary deformation of keratinic fibers, that is, styling agents. Preferred styling agents are styling gels, pump hair sprays, aerosol hair spray, pump hair foams, and aerosol hair foams.

"Styling gels" is the general term, in the context of the present application, for clear or turbid products, styling waxes, styling creams, styling lotions, styling jellies, etc. This term ultimately covers all agents for the styling of hair that are not hair sprays or foams.

"Hair foams" are understood as compositions that form foam upon removal from a suitable container. It may be necessary to add to the agents ingredients that promote foam formation or that stabilize foam once it has been formed. Surfactants and/or emulsifiers, as already described above, are particularly suitable for this. Surfactants from the group of the cationic surfactants are used by preference.

Hair creams and hair gels generally contain structuring agents and/or thickening polymers which serve to impart the desired consistency to the products. Structuring agents and/or thickening polymers are typically used in a quantity from 0.1 to 10 wt %, based on the entire product. Quantities from 0.5 to 5 wt %, in particular 0.5 to 3 wt %, are preferred. Because the polymer combination used according to the present invention has self-thickening properties, however, the addition of further structuring agents and/or thickening polymers is not obligatorily necessary. Preferably, agents according to the present invention contain no further structuring agents and/or thickening polymers.

If agents according to the present invention involve an aerosol product, the latter contains a propellant. Propellants suitable according to the present invention include $N_2O$, dimethyl ether, $CO_2$, air, and alkanes having 3 to 5 carbon atoms, such as propane, n-butane, isobutane, n-pentane, and isopentane, and mixtures thereof. Dimethyl ether, propane, n-butane, isobutane, and mixtures thereof are preferred. The aforesaid alkanes, mixtures of the aforesaid alkanes, or mixtures of the aforesaid alkanes with dimethyl ether are preferably used as the only propellant. The invention also expressly encompasses, however, the concurrent use of propellants of the chlorofluorocarbon type, but in particular the fluorocarbons. For a given spray apparatus, the size of the aerosol droplets or foam bubbles, and the respective size distribution, can be adjusted by the quantitative ratio between propellant and the other constituents of the preparations.

The amount of propellant used varies as a function of the specific composition of the agent, packaging used, and the desired type of product (e.g., hair spray or hair foam). When conventional spray apparatuses are used, aerosol foam products contain propellant preferably in quantities from 1 to 35 wt %, based on total product. Quantities from 2 to 30 wt %, in particular from 3 to 15 wt %, are particularly preferred. Aerosol sprays generally contain larger quantities of propellant. In this case the propellant is used preferably in a quantity from 30 to 98 wt %, based on total product. Quantities from 40 to 95 wt %, in particular from 50 to 95 wt %, are particularly preferred.

Aerosol products can be manufactured in usual fashion. Typically all constituents of the particular agent, with the exception of the propellant, are introduced into a suitable pressure-tight container. The latter is then sealed with a valve. Lastly, the desired quantity of propellant is introduced using conventional techniques.

The present invention is also directed towards a method for temporary deformation of keratinic fibers, involving applying the cosmetic agent according to the present invention onto the hair as a pump hairspray, aerosol hairspray, pump hair foam, aerosol hair foam, or styling gel, and optionally working into the hair using the hand surfaces and/or fingers.

Statements made with regard to the agents according to the present invention apply mutatis mutandis to the method according to the present invention. The desired deformation of the hair can be accomplished using the fingers or hands, and with suitable conventional adjuvants such as, for example, a comb or brush.

A third subject of the invention is the use of agents according to the present invention for the temporary deformation of keratinic fibers. Agents according to the present invention and products containing those agents are notable in particular for imparting a very strong hairstyle hold to the treated hair without thereby making the hair brittle or inflexible. A pleasant, soft feel is instead achieved.

Formulation of the agents can be accomplished in any form usual for cosmetic agents, for example, in the form of solutions that can be applied onto skin or hair as a face or hair lotion or as a pump or aerosol spray, in the form of creams, emulsions, waxes, gels, or also surfactant-containing foaming solutions or other preparations suitable for application to the skin or hair.

EXAMPLES

The following quantitative indications are to be understood, unless otherwise indicated, as percentages by weight. Styling agents A to F according to the present invention were produced in accordance with the following table:

We claim:

1. Cosmetic agent comprising, in a cosmetically acceptable carrier:
   a) at least one copolymer A having at least one structural unit according to formula (I)

at least one structural unit according to formula (II)

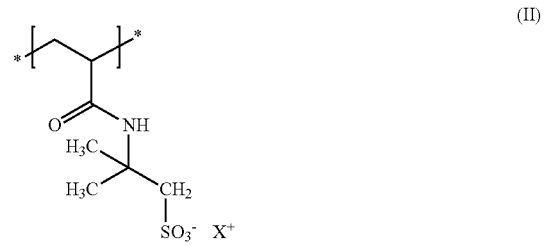

wherein X+ is a physiologically compatible cation, and at least one structural unit according to formula (III)

| Raw materials | A | B | C | D | E | F |
|---|---|---|---|---|---|---|
| Simulgel SMS 88[1] | 3.0 | 3.0 | 3.5 | 5.0 | 3.0 | 3.0 |
| Dow Corning 1403[2] | 3.5 | — | — | — | 3.5 | — |
| Silicone oil, 50 cSt | 2.0 | 2.0 | — | — | 2.0 | 2.0 |
| Dow Corning 949[3] | 1.0 | — | — | — | 1.0 | — |
| Dow Corning 5330[4] | 1.5 | 1.5 | — | — | 1.5 | 1.5 |
| Dow Corning 193 C[5] | — | — | 0.2 | 0.2 | — | — |
| Abil Quat 3272[6] | — | 1.0 | — | — | — | 1.0 |
| Copolymer of vinylpyrrolidone and vinyl acetate, 60% in water | 8.0 | 11.0 | 6.0 | 6.5 | 8.0 | 11.0 |
| Luviset Clear[7] | — | — | 3.0 | 2.75 | — | — |
| Synthalen K[8] | — | — | 1.0 | 1.0 | — | — |
| Phenoxyethanol, methylisothiazolinone (1:1) | — | 0.5 | 0.5 | 0.5 | 0.5 | 0.5 |
| Benzophenone-4 | 0.05 | 0.05 | 0.05 | 0.05 | 0.05 | 0.05 |
| Glycerol, 86% | 6.0 | 6.0 | — | — | 5.0 | 5.0 |
| Dioctyl carbonate | 1.5 | 1.5 | — | — | 1.0 | 1.0 |
| Ethanol, 96% | 15.0 | — | — | — | — | — |
| D-panthenol, 75% | 0.2 | 0.2 | 0.2 | 0.2 | 0.2 | 0.2 |
| Ectoin | — | — | — | — | 0.1 | 0.2 |
| Allantoin | — | — | — | — | 0.1 | 0.1 |
| Caffeine | — | — | — | — | 0.1 | 0.1 |
| Perfume | 0.2 | 0.2 | 0.2 | 0.2 | 0.2 | 0.2 |
| Water, deionized | to 100 | to 100 | to 100 | to 100 | to 100 | to 100 |

[1]Copolymerizate of sodium acrylate, sodium acryloyldimethyltaurate, and dimethylacrylamide (self-invertible inverse latex with isohexadecane and polysorbate-60, approx. 20 wt % solids in water)
[2]Mixture of dimethicone and dimethiconol (INCI name: Dimethicone, Dimethiconol) (Dow)
[3]Amodimethicone with amine numbers (meq amines) of 0.075 to 0.095/g (approx. 35 wt % active substance in water; INCI name: Aminodimethicone, Cetrimonium Chloride, Trideceth-12) (Dow)
[4]Dimethicone copolyol (INCI name: PEG/PPG-15/15 Dimethicone) (Dow)
[5]Dimethicone copolyol (approx. 27 wt % solids in water; INCI name: PEG-12 Dimethicone) (Dow)
[6]Siloxanes and silicones having di-methyl-3-(3-((3-cocoamidopropyl) dimethylammonio)-2-hydroxypropyl)propyl groups, acetates (49 to 51% in propylene glycol; INCI name: Quaternium-80) (Goldschmidt)
[7]Copolymerizate of methacrylamide, N-vinylimidazole, N-vinyl-2-pyrrolidinone (approx. 20 wt % solids in water; INCI name: VP/Methacrylamide/Vinyl Imidazole Copolymer) (BASF)
[8]Polyacrylic acid (solid); INCI name: Carbomer (3V Sigma)

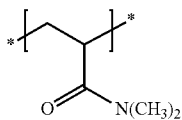
(III)

b) at least one silicone oil and/or silicone gum, and
c) at least one vinyl pyrrolidone/vinyl acetate copolymer.

2. Agent according to claim 1 wherein the at least one copolymer A has a molecular weight of 10 to 750 kDa.

3. Agent according to claim 1 wherein the at least one copolymer A is present in an amount of 0.1 to 10 wt %, based on total weight of the agent.

4. Agent according to claim 1 wherein the at least one copolymer A comprises 10 to 90 mol % monomers of formula (I), 5 to 85 mol % monomers of formula (II) and 5 to 85 mol % monomers of formula (III).

5. Agent according to claim 1 further comprising at least one silicone of formula Si-I $$(CH_3)_3Si—[O—Si(CH_3)_2]_x—O—Si(CH_3)_3 \quad (Si-I)$$

wherein x is a number from 0 to 100.

6. Agent according to claim 1 further comprising at least one aminofunctional silicone of formula (Si-II)

$$R'_a G_{3-a}\text{-}Si(OSiG_2)_n\text{-}(OSiG_b R'_{2-b})_m—O—SiG_{3-a}\text{-}R'_a \quad (Si—II),$$

wherein
G is —H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—CH($CH_3$)$CH_2CH_3$, —CH($CH_3$)$CH_2CH_3$, —O—C($CH_3$)$_3$, or —C($CH_3$)$_3$;
a is a number from 0 to 3;
b is a number from 0 to 1;
m and n are numbers whose sum (m+n) is from 1 to 2000, wherein n is a value from 0 to 1999 and m is a value from 1 to 2000;
R' is a monovalent residue chosen from -Q-N(R")—$CH_2$—$CH_2$—N(R")$_2$, -Q-N(R")$_2$, -Q-$N^+$(R")$_3A^-$, -Q-$N^+$H(R")$_2A^-$, -Q-$N^+$H$_2$(R")A", or -Q-N(R")—$CH_2$—$CH_2$—$N^+$R"H$_2A^-$; where Q is a chemical bond, —$CH_2$—, —$CH_2$—$CH_2$—, —$CH_2CH_2CH_2$—, —C($CH_3$)$_2$—, —$CH_2CH_2CH_2CH_2$—, —$CH_2C(CH_3)_2$—, or —CH($CH_3$)$CH_2CH_2$—, R" is identical or different residues chosen from —H, phenyl, benzyl, —$CH_2$—CH($CH_3$)Ph and $C_{1-20}$ alkyl residues, and A is an anion.

7. Agent according to claim 1 further comprising at least one aminofunctional silicone of formula (Si-IIa)

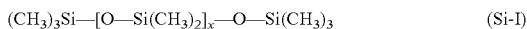
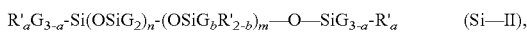
(Si-IIa)

wherein m and n are numbers whose sum (m+n) is from 1 to 2000, preferably from 50 to 150, n being a value from 0 to 1999, and m being a value from 1 to 2000.

8. Agent according to claim 1 further comprising at least one aminofunctional silicone of formula (Si-IIb)

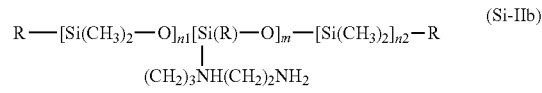
(Si-IIb)

wherein R is —OH, —O—$CH_3$, or a —$CH_3$ group, and m, n1, and n2 are numbers whose sum (m+n1+n2) is from 1 to 2000, the sum (n1+n2) is a value from 0 to 1999, and m is a value from 1 to 2000.

9. Agent according to claim 1 further comprising at least one copolymer B according to either or both of the following formulae

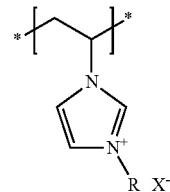
(B-I)

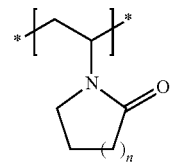
(B-II)

wherein
R is a $C_1$ to $C_{30}$ alkyl group, a $C_1$ to $C_4$ aralkyl group, a $C_2$ to $C_6$ alkenyl group, or a $C_2$ to $C_6$ hydroxyalkyl group,
$X^-$ is a physiologically compatible anion, and
n is 2 or 3 as the number of methylene units.

10. Agent according to claim 1 further comprising at least one acrylate polymer C chosen from c1) polyacrylic acid and/or c2) copolymers of methacrylic acid with acrylamidopropanesulfonic acid and/or c3) copolymers of acrylic acid with methacrylic acid and acrylic acid esters and/or c4) copolymers of acrylic acid with methacrylic acid with acrylic acid esters and methacrylic acid esters and/or c5) copolymers of acrylic acid esters with methacrylic acid.

11. Agent according to claim 1 further comprising at least one copolymer E chosen from at least one monomer e1 chosen from acrylic acid and/or methacrylic acid, and at least one monomer e2 chosen from acrylamide and/or methacrylamide, and at least one monomer e3 chosen from N-substituted acrylamides and/or methacrylamides.

12. Agent according to claim 1 further comprising at least one copolymer F chosen from f1) copolymers of vinylpyrrolidone with methacrylamidopropyltrimethylammonium chloride (MAPTAC) and/or f2) copolymers of vinylpyrrolidone with dimethylaminoethyl methacrylate and/or f3) copolymers of vinylpyrrolidone with dimethylaminopropylmethacrylamide and alkyldimethylpropylmethacrylamide ammonium salts.

13. Agent according to claim 1, wherein the agent is a styling gel, a pump hairspray, an aerosol hairspray, a pump hair foam, or an aerosol hair foam.

14. Method for the temporary deformation of keratinic fibers comprising applying a cosmetic agent according to claim 1 onto hair using a pump hairspray, aerosol hairspray, pump hair foam, aerosol hair foam, or styling gel, and optionally working the agent into the hair using hand surfaces and/or fingers.

* * * * *